United States Patent
Reed et al.

(10) Patent No.: US 10,573,404 B2
(45) Date of Patent: Feb. 25, 2020

(54) SYSTEMS AND METHODS FOR DETERMINING FLUX DISTRIBUTION

(71) Applicant: WISCONSIN ALUMNI RESEARCH FOUNDATION, Madison, WI (US)

(72) Inventors: Jennifer Leanne Reed, Madison, WI (US); Matthew Ray Long, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 907 days.

(21) Appl. No.: 15/015,561

(22) Filed: Feb. 4, 2016

(65) Prior Publication Data

US 2016/0232278 A1 Aug. 11, 2016

Related U.S. Application Data

(60) Provisional application No. 62/112,727, filed on Feb. 6, 2015.

(51) Int. Cl.
*G16B 5/00* (2019.01)

(52) U.S. Cl.
CPC ....................... *G16B 5/00* (2019.02)

(58) Field of Classification Search
None
See application file for complete search history.

(56) References Cited

PUBLICATIONS

Lee et al. (Genome Informatics (2003) vol. 14:23-33).*
Mahadevan et al. (Metabolic Engineering (2003) vol. 5:264-276).*
Becker et al., Context-specific metabolic networks are consistent with experiments. Sauro HM, editor. PLoS Comput Biol. Public Library of Science; May 2008; 4(5):e1000082, 10 pages.
Blazier et al., Integration of expression data in genome-scale metabolic network reconstructions. Front Physiol. Aug. 6, 2012;3:299, 7 pages.
Burgard et al., Flux coupling analysis of genome-scale metabolic network reconstructions. Genome Res. Cold Spring Harbor Laboratory Press; Mar. 1, 2004; 14(2):301-12.
Chandrasekaran et al., Probabilistic integrative modeling of genome-scale metabolic and regulatory networks in *Escherichia coli* and *Mycobacterium tuberculosis*. Proc Natl Acad Sci U S A. Oct. 12, 2010; 107(41):17845-50.
Chowdhury et al., k-OptForce: integrating kinetics with flux balance analysis for strain design. PLoS Comput Biol. Feb. 20, 2014;10(2):e1003487, 18 pages.
Covert et al., Integrating metabolic, transcriptional regulatory and signal transduction models in *Escherichia coli*. Bioinformatics. Sep. 15, 2008; 24(18):2044-50.
Griffin et al., Complementary Profiling of Gene Expression at the Transcriptome and Proteome Levels in *Saccharomyces cerevisiae*. Mol Cell Proteomics. Apr. 2, 2002; 1(4):323-33.
Ishii et al., Multiple high-throughput analyses monitor the response of *E. coli* to perturbations. Science. Apr. 27, 2007;316(5824):593-7.
Kim et al., RELATCH: relative optimality in metabolic networks explains robust metabolic and regulatory responses to perturbations. Genome Biol. Jul. 5, 2012;13(9):R78, 12 pages.
Kim et al., Metabolic network modeling and simulation for drug targeting and discovery. Biotechnol J. Mar. 29, 2012;7(3):330-42.
Lewis et al., Omic data from evolved *E. coli* are consistent with computed optimal growth from genome-scale models. Mol Syst Biol. Jul. 2010;6:390, 13 pages.
Liu et al., A constraint-based model of Scheffersomyces stipitis for improved ethanol production. Biotechnol Biofuels. BioMed Central; Sep. 21, 2012; 5(1):72.
Machado et al., Systematic evaluation of methods for integration of transcriptomic data into constraint-based models of metabolism. Maranas CD, editor. PLoS Comput Biol. Public Library of Science; Apr. 2014; 10(4):e1003580, 12 pages.
Mahadevan et al., The effects of alternate optimal solutions in constraint-based genome-scale metabolic models. Metab Eng. 2003; 5(4):264-76.
Montezano et al., Flux Balance Analysis with Objective Function Defined by Proteomics Data—Metabolism of *Mycobacterium tuberculosis* Exposed to Mefloquine. Bourdon J, editor. PLoS One. Public Library of Science; Jul. 28, 2015; 10(7):e0134014, 19 pages.
Orth et al., A comprehensive genome-scale reconstruction of *Escherichia coli* metabolism—2011. Mol Syst Biol. Oct. 11, 2011;7:535, 9 Pages.
Orth et al., What is flux balance analysis? Nat Biotechnol. Nature Publishing Group; Mar. 2010; 28(3):245-8.
Reed et al., an expanded genome-scale model of *Escherichia coli* K-12 (iJR904 GSM/GPR). Genome Biol. 2003;4(9):R54, 12 pages.
Segrè et al., Analysis of optimality in natural and perturbed metabolic networks. Proc Natl Acad Sci U S A. Nov. 12, 2002;99(23):15112-7.

(Continued)

*Primary Examiner* — Lori A. Clow
(74) *Attorney, Agent, or Firm* — Daniel A. Blasiole; DeWitt LLP

(57) ABSTRACT

Provided are systems and methods for accurately determining flux distribution in organisms or cells without use of metabolic flux analysis data. The methods include estimating flux distributions in multiple reference strains (variants of a parental strain) using experimentally determined extracellular flux data from the reference strains, and determining a flux distribution for the parental strain from the estimated flux distributions for the reference strains and from experimentally measured extracellular fluxes for the parental strain. The systems are configured for carrying out the methods.

3 Claims, 9 Drawing Sheets

(56) References Cited

PUBLICATIONS

Shlomi et al., Regulatory on/off minimization of metabolic flux changes after genetic perturbations. Proc Natl Acad Sci U S A. May 24, 2005;102(21):7695-700.

Zamboni et al., 13C-based metabolic flux analysis. Nat Protoc. Jan. 2009; 4(6):878-92.

* cited by examiner

SYSTEMS AND METHODS FOR DETERMINING FLUX DISTRIBUTION

STATEMENT REGARDING FEDERALLY SPONSORED RESEARCH

This invention was made with government support under DE-SC0008103 awarded by the US Department of Energy. The government has certain rights in the invention.

FIELD OF THE INVENTION

The invention is directed to systems and methods for determining and predicting flux distribution in organisms, such as microorganisms.

BACKGROUND

Extracellular fluxes and gene expression data are easily measured and have been obtained for a wide variety of organisms and applications. However, it is difficult to incorporate these data directly into computational models to predict intracellular flux distributions. Central metabolic fluxes can instead be quantified using carbon isotope-based (i.e., $^{13}C$) metabolic flux analysis (MFA). MFA data, however, can be costly to obtain directly, and published data is available for only a few organisms.

Flux balance analysis (FBA) is a mathematical method for simulating metabolism in genome scale reconstructions of metabolic networks. FBA is often used to predict flux distributions that maximize biomass, and parsimonious FBA (pFBA) predicts flux distributions that additionally minimize the sum total of metabolic fluxes. When compared to MFA, FBA is less intensive in terms of the input data required for constructing the model (i.e., does not require $^{13}C$-based pathway fluxes), is computationally inexpensive, and can calculate steady-state metabolic fluxes for large models in just a few seconds. However, FBA predictions do not always match experimentally measured fluxes.

FBA is also used in bioprocess engineering to systematically identify modifications to the metabolic networks of microbes used in fermentation processes that improve product yields of industrially important chemicals (e.g., ethanol, succinic acid, etc.). When simulating knockouts or growth on media, FBA predicts a steady-state flux distribution that is more consistent with adaptively evolved strains, which can be reached over varying timescales (e.g., 40 days, 700 generations, etc.). Alternatives to FBA—including MOMA, ROOM, and RELATCH—can better predict the immediate effect of an environmental perturbation or gene deletion. While more accurate, these FBA alternatives rely heavily upon the flux estimates for the parental strain. As a result, incorrect parental strain fluxes (i.e., starting point) can lead to significant errors in estimates for mutants derived from the parental strain. A need exists for a method with improved identification of parental strain fluxes that does not require MFA.

Systems and methods that address the above-mentioned problems are needed.

SUMMARY OF THE INVENTION

The present invention is a constraint-based modeling approach to calculate extracellular and intracellular flux distributions in a parental strain using easily obtained experimental data from a small set of reference strains (usually gene knockout mutants) derived from the parental strain. By incorporating growth rates, uptake and secretion rates (i.e., extracellular fluxes), and optional gene expression data for multiple reference strains and the parental strain into a constraint-based metabolic model, the present invention more accurately predicts the flux distribution in the parental strain. This parental strain flux distribution can then be used with existing computational methods (e.g., MOMA, ROOM, and RELATCH) to predict fluxes in newly derived strains (uncharacterized strains that were not included as reference strains) with greater accuracy, thus improving computational strain design for metabolic engineering applications.

The methods described herein improve parental strain flux estimations by as much as ~60% compared to other approaches (pFBA or RELATCH), where accuracy was measured against MFA data in *E. coli*.

One aspect of the invention comprises a method for determining flux distribution in a parental strain and, optionally, in a derived strain thereof. The method comprises estimating, in a computer system, a flux distribution from experimentally measured extracellular fluxes for each of a plurality of reference strains having known modifications with respect to the parental strain, wherein the flux distribution for each reference strain comprises a directional, quantitative set of fluxes corresponding to a set of reactions occurring in the reference strain. The method further comprises determining, in a computer system, a flux distribution for the parental strain from the estimated flux distributions for the reference strains and experimentally measured extracellular fluxes for the parental strain, wherein the flux distribution for the parental strain comprises a directional, quantitative set of fluxes corresponding to a set of reactions occurring in the parental strain.

In some versions, determining the flux distribution for the parental strain comprises minimizing the sum-squared difference between estimated fluxes for the parental strain and the experimentally measured extracellular fluxes for the parental strain, the sum-squared difference being scaled by the number of experimentally measured extracellular fluxes in the parent strain.

In some versions, determining the flux distribution for the parental strain comprises minimizing the sum-squared difference between estimated fluxes for the parental strain and fluxes in the estimated flux distribution for the reference strains, the sum-squared difference being scaled by the number of estimated fluxes and the number of reference strains in the plurality of reference strains. The number of estimated fluxes is the same for the parental strain and each of the reference strains.

In some versions, determining the flux distribution for the parental strain comprises minimizing the sum-squared difference between estimated fluxes for the parental strain and the experimentally measured extracellular fluxes for the parental strain, the sum-squared difference being scaled by the number of experimentally measured extracellular fluxes in the parent strain, and further comprises minimizing the sum-squared difference between estimated fluxes for the parental strain and fluxes in the estimated flux distribution for the reference strains, the sum-squared difference being scaled by the number of estimated fluxes and the number reference strains in the plurality of reference strains. The number of estimated fluxes is the same for the parental strain and each of the reference strains. In some versions, the sum-squared difference between the estimated fluxes for the parental strain and the experimentally measured extracellular fluxes for the parental strain is scaled with respect to the sum-squared difference between the estimated fluxes for the parental strain and fluxes in the estimated flux distribution for the reference strains by a factor of from about 0.0000001 to about 10,000,000, from about 0.000001 to about 1,000,000, from about 0.00001 to about 100,000, from about 0.0001 to about 10,000, from about 0.001 to about 1,000, from about 0.01 to about 100, or from about 0.1 to about 10. Values above and below these factors may be acceptable. In some versions, the respective sum-squared differences are scaled by a factor of 1. In some versions, the respective sum-squared differences are scaled by a factor other than 1.

In some versions, the method further comprises estimating enzyme contributions for each of the plurality of reference strains from experimentally measured gene expression values for each of the plurality of reference strains and determining enzyme contributions in the parental strain from the estimated enzyme contributions of the plurality of reference strains and experimentally measured gene expression values for the parental strain. An enzyme contribution is a maximum capacity of an enzyme to contribute to total flux through one or more of reactions in a set of reactions occurring in a particular strain. In some versions, the method further comprises experimentally measuring at least one of the gene expression values. In some versions, the method comprises experimentally measuring all or nearly all of the gene expression values.

In some versions, the known modifications of the reference strains comprise genetic modifications.

In some versions, the method further comprises experimentally measuring at least one of the extracellular fluxes in at least a subset of the reference strains. In some versions, the method comprises experimentally all or nearly all of the extracellular fluxes in all or nearly all of the reference strains.

In some versions, the method further comprises generating at least a subset of the reference strains.

In some versions, the method further comprises experimentally measuring at least one of the extracellular fluxes in the parental strain. In some versions, the method comprises experimentally measuring all or nearly all of the extracellular fluxes in the parental strain.

In some versions, the method further comprises predicting a flux distribution for an uncharacterized strain (i.e., derived strain) having a modification with respect to the parental strain, wherein the uncharacterized strain is not one of the reference strains. The modification in the uncharacterized strain may comprise a genetic modification. The method may further comprise generating the uncharacterized strain.

Another aspect of the invention is a system for determining flux distribution in a parental strain and, optionally, in a derived strain thereof. The system comprises a first module in a computer system, the first module being configured to estimate a flux distribution from experimentally measured extracellular fluxes for each of a plurality of reference strains having known modifications with respect to the parental strain, wherein the flux distribution for each reference strain comprises a directional, quantitative set of fluxes corresponding to a set of reactions occurring in the reference strain. The system further comprises a second module in a computer system, the second module being configured to determine a flux distribution for the parental strain from the estimated flux distributions for the reference strains and experimentally measured extracellular fluxes for the parental strain, wherein the flux distribution for the parental strain comprises a directional, quantitative set of fluxes corresponding to a set of reactions occurring in the parental strain. The system can optionally contain a third module that is configured to predict a flux distribution in a strain derived from the parental strain, using estimated flux distributions for the parental strain.

In some versions, the second module is configured to minimize the sum-squared difference between estimated fluxes for the parental strain and the experimentally measured extracellular fluxes for the parental strain, the sum-squared difference being scaled by the number of experimentally measured extracellular fluxes in the parent strain.

In some versions, the second module is configured to minimize the sum-squared difference between estimated fluxes for the parental strain and fluxes in the estimated flux distribution for the reference strains, the sum-squared difference being scaled by the number of estimated fluxes and the number of reference strains in the plurality of reference strains.

In some versions, the second module is configured to minimize the sum-squared difference between estimated fluxes for the parental strain and the experimentally measured extracellular fluxes for the parental strain, the sum-squared difference being scaled by the number of experimentally measured extracellular fluxes in the parent strain, and further to minimize the sum-squared difference between estimated fluxes for the parental strain and fluxes in the estimated flux distribution for the reference strains, the sum-squared difference being scaled by the number of estimated fluxes and the number reference strains in the plurality of reference strains. In some versions, the second module is configured to scale the sum-squared difference between the estimated fluxes for the parental strain and the experimentally measured extracellular fluxes for the parental strain with respect to the sum-squared difference between fluxes in the estimated flux distribution for the reference strains and the estimated fluxes for the parental strain by a factor of from about 0.0000001 to about 10,000,000, from about 0.000001 to about 1,000,000, from about 0.00001 to about 100,000, from about 0.0001 to about 10,000, from about 0.001 to about 1,000, from about 0.01 to about 100, or from about 0.1 to about 10. Values above and below these factors may be acceptable. In some versions, the second module is configured to scale the respective sum-squared differences by a factor of 1. In some versions, the second module is configured to scale the respective sum-squared differences by a factor other than 1.

In some versions, the first and second modules are further configured to estimate enzyme contributions for each of the plurality of reference strains from experimentally measured gene expression values for each of the plurality of reference strains, and to determine enzyme contributions in the parental strain from the estimated enzyme contributions of the plurality of reference strains and experimentally measured gene expression values for the parental strain.

The objects and advantages of the invention will appear more fully from the following detailed description of the preferred embodiment of the invention made in conjunction with the accompanying drawings.

DETAILED DESCRIPTION OF THE INVENTION

Figure 1:
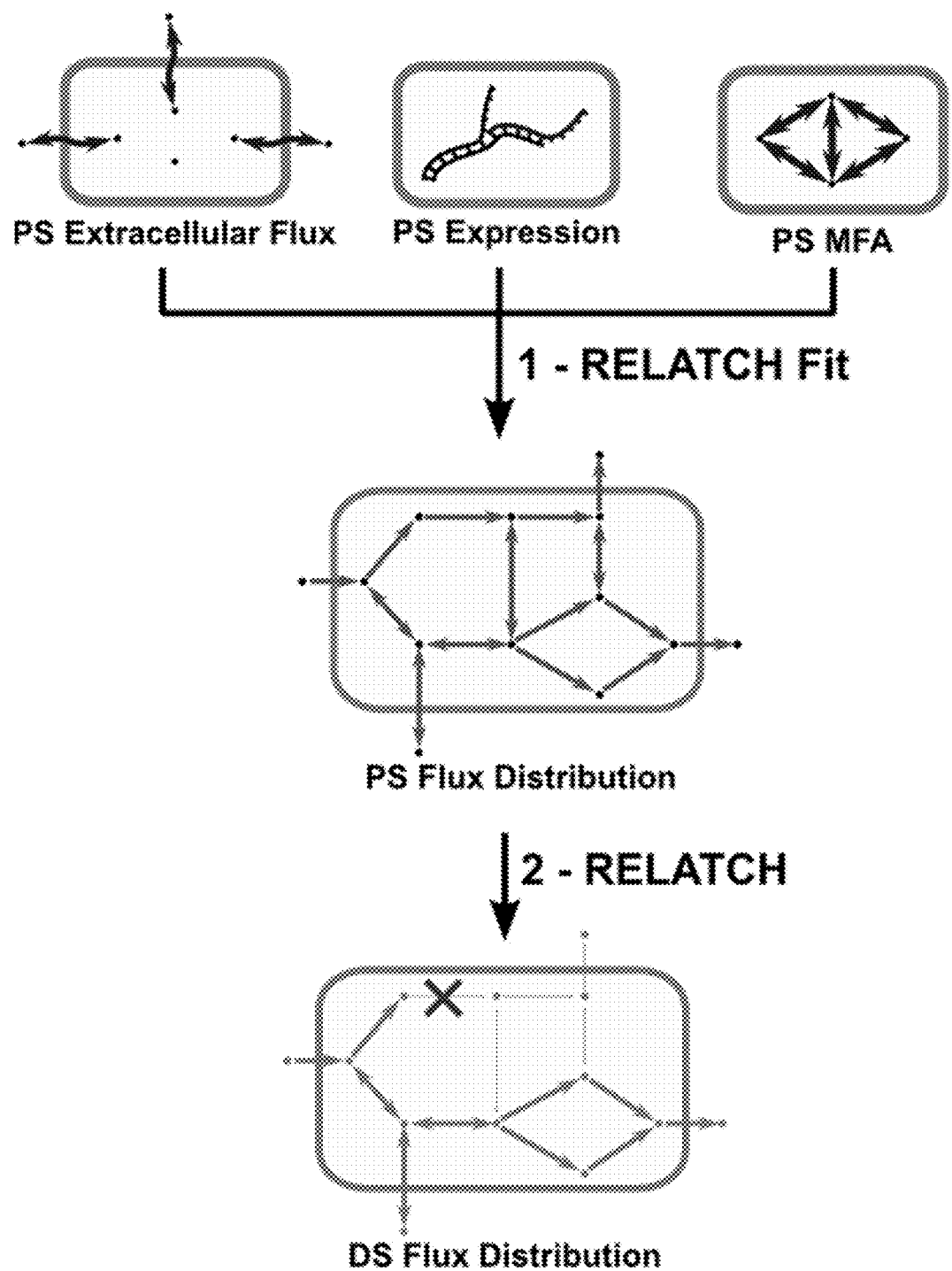
FIG. 1 is a schema depicting a methods of the prior art for utilizing MFA, gene expression, and extracellular flux data to accurately calculate the parental strain (PS) flux distribution and then calculating new knockout or derived strains (DS) therefrom.

A schematic of exemplary prior art methods for calculating parental flux distributions in a parental strain and predicting flux distributions in knockout strains is shown in FIG. 1. Parental flux distributions can first be calculated using gene expression data, extracellular flux data, and metabolic flux analysis data for the parental strain (wild-type strain in FIG. 1) using the RELATCH Fit program (Kim et al. 2012). Once the parental flux distributions are calculated, flux distribution in evolved or un-evolved derived strains (new, uncharacterized modified versions of the parent strain) can then be determined using the RELATCH program (Kim et al. 2012). A problem with such methods is that they rely fundamentally on the metabolic flux analysis data in the RELATCH Fit program. Attempting to predict flux distributions for derived strains of parental strains using parental flux distributions calculated in the absence of metabolic flux analysis data can result in error.

The present invention provides systems and methods for calculating parental flux distributions and determining flux distributions of new derived strains in the absence of metabolic flux analysis data and, optionally in the absence of gene expression data. A schema of an exemplary method is provided in FIG. 2.

A first step involves estimating the flux distribution for each of a plurality of reference strains. The reference strains include various modified versions of a parental strain. The modified versions may include gene-knockout mutants, mutants that have partial activity of certain enzymes, strains grown in modified environmental conditions (e.g., different oxygen concentration), or strains that are treated with agents that elicit certain physiological effects, such as inhibiting the function of an enzyme.

The flux distribution for each reference strain may be estimated using any of a number of suitable programs or methods. Exemplary programs or methods include RELATCH Fit, flux balance analysis, and parsimonious flux balance analysis (pFBA) (Lewis et al. 2010), among others. Input data used in estimating the reference strain flux distribution preferably includes experimentally measured fluxes (see Blazier et al. 2012) for each of the reference strains. The experimentally measured fluxes generally comprise extracellular fluxes. In some versions, the experimentally measured fluxes consist of extracellular fluxes.

Once the flux distribution for each of the reference strains is estimated, a second step involves determining a flux distribution for the parental strain. Information used for determining the flux distribution for the parental strain preferably includes experimentally measured fluxes for the parental strain as well as the estimated flux distributions from the reference strains. The experimentally measured fluxes preferably comprise extracellular fluxes. In some versions, the experimentally measured fluxes consist of extracellular fluxes. In preferred versions of the invention, metabolic flux analysis data is not used in determining the flux distribution for the parental strain. In some versions, gene expression data also is not used.

The flux distribution for the parental strain can be determined by matching the predicted fluxes for the parent strain as closely as possible to the experimentally measured fluxes for the parent strain and to the estimated flux distributions from the reference strains. This can be performed by minimizing the sum-squared difference between the estimated extracellular fluxes for the parental strain and the experimentally measured extracellular fluxes for the parental strain, as well as minimizing the sum-squared difference between the estimated fluxes for the parental strain and fluxes in the estimated flux distributions for the reference strains. The sum-squared difference between the estimated extracellular fluxes for the parental strain and the experimentally measured extracellular fluxes for the parental strain may be scaled by the number of experimentally measured extracellular fluxes in the parent strain. The sum-squared difference between estimated fluxes for the parental strain and fluxes in the estimated flux distribution for the reference strains may be scaled by the number of estimated fluxes in the parent strain and by the number reference strains in the plurality of reference strains. Furthermore, the sum-squared difference between the estimated extracellular fluxes for the parental strain and the experimentally measured extracellular fluxes for the parental strain may be scaled with respect to the sum-squared difference between fluxes in the estimated flux distribution for the reference strains and estimated fluxes for the parental strain. This may be done to emphasize the relationship of the estimated fluxes of the parental strain to either the experimentally measured extracellular fluxes for the parental strain or the estimated flux distributions of the reference strains. Equations for carrying out these processes are provided by Equations 11a-11e in Example 2 below.

Once the flux distribution for the parental strain is determined, a third, optional, step involves predicting flux distributions in one or more uncharacterized, modified versions (i.e., "derived strains") of the parental strain. The derived strains may include gene-knockout mutants, mutants that have partial activity of certain enzymes, strains grown in modified environmental conditions, or strains that are treated with agents that elicit certain physiological effects, such as inhibiting the function of an enzyme. The modifications in the uncharacterized, modified versions of the parental strain are preferably different from the modifications that characterize the reference strains. Exemplary programs or methods for predicting the flux distributions in the uncharacterized, modified versions of the parental strain include pFBA, MOMA (Segre et al. 2002), RELATCH (Kim et al. 2012), and ROOM (Shlomi et al. 2005), among others.

In some versions of the invention, the first step involves estimating the flux distribution and enzyme contributions within the flux distribution for each of the plurality of reference strains. Programs or methods such as RELATCH Fit are capable of estimate flux distributions as well as enzyme contributions. Input data used in estimating the flux distribution may include experimentally measured fluxes and gene expression data (see Blazier et al. 2012) for each of the reference strains.

Similarly, the second step may involve determining a flux distribution and enzyme contributions for the parental strain. Input data for determining the flux distribution and enzyme contributions for the parental strain may include the estimated flux distributions and enzyme contributions from the reference strains as well as experimentally measured fluxes and gene expression data for the parental strain. Programs or methods for determining the flux distribution and enzyme contributions are provided in Example 1 below.

Determining the flux distribution and enzyme contributions for the parental strain may comprise minimizing enzyme contribution directional violation terms from reference strains in which a change in an enzyme contribution between the parental strain and a given reference strain is in the opposite direction compared to a change in the experimentally measured gene expression values between the parental strain and the given reference strain. If the change in an enzyme contribution between the parental strain and a given reference strain is in an opposite direction compared to a change in the experimentally measured gene expression values between the parental strain and the given reference strain, the associated enzyme contribution directional violation term preferably becomes positive and is penalized in an objective function comprising the enzyme contribution directional violation term of the given reference strain. If the change in the enzyme contribution between the parental strain and a given reference strain is in the same direction compared to a change in the experimentally measured gene expression values between the parental strain and the given reference strain, the associated enzyme contribution directional violation term preferably becomes zero and does not affect the value of the objective function. In some versions, proteomics (i.e., protein levels) can be used in place of or in addition to gene expression data, wherein the protein levels are used analogously to the gene expression levels.

Some versions of the invention comprise experimentally measuring the gene expression values in reference strains and/or the parental strain. Methods of measuring gene expression are well-known in the art. Any method of measuring gene expression is suitable in the present invention.

Some versions of the invention comprise generating reference strains and/or uncharacterized, modified versions of the parental strain (e.g., "derived strains"). In some versions, the reference strains or uncharacterized, modified versions of the parental strain include genetic modifications. Genetic engineering of organisms is well-known in the art. Any methods of genetically modifying the parental strains to obtain the reference strains or uncharacterized, modified versions of the parental strain are suitable in the present invention.

As used herein, "strain" refers to any unique type of individual cell or collection of cells. Non-limiting examples of individual cells include microorganisms or isolated cells from organs or tissues. Non-limiting examples of collections of cells include organs or tissues.

As used herein the term "parental strain" or "parent strain" refers to a strain from which all reference and derived strains are derived. The parental strain is chosen so that any and all reference and derived strains may be obtained from it via modification, such as genetic modification (i.e., gene deletion, gene insertion, gene transformation via an extra-chromosomal plasmid, etc.).

As used herein the term "reference strain" refers to a modified version of the parental strain. The modification is preferably a genetic modification. Experimental data for the reference strains may be used to calculate a reference strain's flux distribution and with other reference strains may be further used to estimate fluxes in the parental strain.

As used herein the term "derived strain" refers to a new, uncharacterized modified version of the parental strain. The modification is preferably a genetic modification. The derived strain should not be one of the reference strains. Derived strain flux distributions can be predicted from the parental strain's flux distribution.

As used herein, "modified" or "modification" used with reference to a strain (parental strain, reference strain, or derived strain) refers to any structural change or treatment that affects the abundance of a gene product in a cell. Preferred modifications include genetic modifications. The genetic modifications may entirely delete a gene (and its corresponding gene product), decrease the abundance of a gene product, decrease the activity of a gene product, increase the activity of a gene product, increase the abundance of a gene product, or add an entire new gene. The genetic modifications may occur through mutation of the strain's chromosome or through ectopic introduction of extrachromosomal material (e.g., plasmids, etc.). Other modifications may include small-molecule treatments that either increase or decrease expression of a gene product or increase or decrease its activity through allosteric regulation or other mechanisms ($V_{max}$, $K_m$, etc.). Additionally, modification of the environmental growth conditions (e.g., temperature, oxygen concentration, etc.) may also increase or decrease expression of a gene product.

Methods and systems for constructing and analyzing steady-state in silico models of biological networks are provided herein. A steady-state model can be used to simulate different aspects of cellular behavior of cells under different environmental and genetic conditions, thereby providing valuable information for a range of industrial and research applications. Developing steady-state models of biological networks can be used to inform and guide the research process, potentially leading to the identification and production of new enzymes, medicines or metabolites of commercial importance.

As used herein, the term "concentration" refers to a numerical value with physical units of mass*volume$^{-1}$, such as molar and millimolar. Such quantities include but are not limited to molecules in a biochemical network, such as glucose, pyruvate, lactate, enzymes that carry out biochemical transformations or transport reactions such as hexokinase, adenosine deaminase, and sodium-potassium ATPase pump.

As used herein, the term "mass balance" refers to a linear algebraic equation which equates the net production rate and net consumption rate for each component in a specified biological network.

As used herein the term "flux" or "reaction flux" refers to a single flux in a flux distribution. Individual fluxes can be represented as the difference between a forward and reverse flux, with units mass, or number of moles, or number of molecules per unit biomass per unit time.

As used herein the term "extracellular flux" refers to the growth, uptake or secretion rate of one or more metabolites by a strain. The extracellular fluxes may be experimentally measured by monitoring media concentrations over time, and most have units of mass, moles, or number of molecules per unit biomass per unit time. Growth rate has units of inverse unit time.

As used herein the term "intracellular flux" refers to the flux through one or more reactions taking place in a cell (e.g. transport or enzymatic reactions). The intracellular fluxes represent the net difference between a forward and reverse flux, with units of mass, moles, or number of molecules per unit biomass per unit time. Intracellular fluxes can be measured experimentally with the use of carbon isotope-based metabolic flux analysis (MFA).

As used herein, the term "flux distribution" refers to a directional, quantitative set of values corresponding to the set of reactions in a network, representing the mass flow per unit biomass per unit time for each reaction in the network being analyzed.

As used herein the term "enzyme contribution" refers to the maximum capacity of a particular enzyme to contribute to the total flux through a reaction in a strain. Enzyme contributions have the same units as flux, and most have units of mass, moles, or number of molecules per unit biomass per unit time.

As used herein, the term "biological network" refers to assembled reactions reflecting biological processes. Examples of biological networks include but are not limited to metabolic networks, signaling networks, and regulatory networks.

As used herein, the term "network map" refers to the set of reactions in the biological network and the compounds, macromolecules, and/or genes with which they are associated.

As used herein, the term "stoichiometric matrix" or "S" refers to a matrix with the stoichiometric coefficients for reactions represented by the columns and the substrates and products in the rows. The stoichiometric matrix may be written for any biological network. Examples include but are not limited to metabolic networks and signaling networks.

As used herein, the term "steady-state" refers to any of a number of conditions for which the flux distribution and concentrations do not change over time. Equilibrium is a special case which also satisfies the steady-state. In general, unless otherwise specified, references to the steady-state imply a non-equilibrium steady-state.

The reconstruction of a genome-scale reaction network (network map) requires the identification of all its chemical components and the chemical transformations that they participate in. This process primarily relies on annotated genomes and detailed bibliomic assessment. See Reed, et al. (2006), *Nature Reviews Genetics,* 7(2):130-141, which is hereby incorporated by reference in its entirety. See also, U.S. Pat. No. 8,301,393 which is also incorporated by reference in its entirety. The result of this process is the stoichiometric matrix, S, that is used in the mass balances $$S \cdot v = 0$$

that are the basis of all steady-state models. Here v is the vector of the reaction fluxes (i.e., flux distribution). All biochemical transformations are fundamentally uni- or bi-molecular and their reaction rates can be represented by mass action kinetics, or generalizations thereof. The net reaction flux for every reaction in a network can be represented by the difference between a forward and reverse flux. This commonly used formulation is based on several well-known assumptions, such as constant temperature, volume, and homogeneity of the medium. A steady-state flux distribution (v) must satisfy the mass balances.

The availability of genomic and bibliomic data can be used to define S, which has been described in detail. S is primarily derived from an annotated genomic sequence fortified with any direct bibliomic data on the organisms' gene products. In the physico-chemical context, S represents chemistry (i.e. stoichiometry of reactions). In the biological and genetic considerations context, the matrix S is reconstructed based on the content of a genome and is a property of a species.

As used herein, the term "reaction" is intended to mean a conversion that consumes a substrate or forms a product that occurs in a biological network. The term can include a conversion that occurs due to the activity of one or more enzymes that are genetically encoded by an organism's genome. The term can also include a conversion that occurs spontaneously. Conversions included in the term include, for example, changes in chemical composition such as those due to nucleophilic or electrophilic addition, nucleophilic or electrophilic substitution, elimination, isomerization, deamination, phosphorylation, methylation, glycosylation, reduction, oxidation or changes in location such as those that occur due to a transport reaction that moves one or more reactants within the same compartment or from one cellular compartment to another. In the case of a transport reaction, the substrate and product of the reaction can be chemically the same and the substrate and product can be differentiated according to location in a particular cellular compartment. Thus, a reaction that transports a chemically unchanged reactant from a first compartment to a second compartment has as its substrate the reactant in the first compartment and as its product the reactant in the second compartment. It will be understood that when used in reference to an in silico model or data structure, a reaction is intended to be a representation of a chemical conversion that consumes a substrate or produces a product.

As used herein, the term "reactant" is intended to mean a chemical that is a substrate or a product of a reaction that occurs in a biological network. The term can include substrates or products of reactions performed by one or more enzymes encoded by gene(s), reactions occurring in cells that are performed by one or more non-genetically encoded macromolecule, protein or enzyme, or reactions that occur spontaneously in a cell. Metabolites are understood to be reactants within the meaning of the term. It will be understood that when used in reference to an in silico model or data structure, a reactant is intended to be a representation of a chemical that is a substrate or a product of a reaction that occurs in a cell.

As used herein the term "substrate" is intended to mean a reactant that can be converted to one or more products by a reaction. The term can include, for example, a reactant that is to be chemically changed due to nucleophilic or electrophilic addition, nucleophilic or electrophilic substitution, elimination, isomerization, deamination, phosphorylation, methylation, reduction, oxidation or that is to change location such as by being transported across a membrane or to a different compartment.

As used herein, the term "product" is intended to mean a reactant that results from a reaction with one or more substrates. The term can include, for example, a reactant that has been chemically changed due to nucleophilic or electrophilic addition, nucleophilic or electrophilic substitution, elimination, isomerization, deamination, phosphorylation, methylation, reduction or oxidation or that has changed location such as by being transported across a membrane or to a different compartment.

As used herein, the term "stoichiometric coefficient" is intended to mean a numerical constant correlating the number of one or more substrates and the number of one or more products in a chemical reaction. Typically, the numbers are integers as they denote the number of molecules of each reactant in an elementally balanced chemical reaction that describes the corresponding conversion. However, in some cases the numbers can take on non-integer values, for example, when used in a lumped reaction or to reflect empirical data.

As used herein, the term "plurality" in intended to mean at least 2. For example, the term "plurality," when used in reference to reactions or reactants, is intended to mean at least 2 reactions or reactants. The term can include any number of reactions or reactants in the range from 2 to the number of naturally occurring reactants or reactions for a particular cell. Thus, the term can include, for example, at least 10, 20, 30, 50, 100, 150, 200, 300, 400, 500, 600 or more reactions or reactants. The number of reactions or reactants can be expressed as a portion of the total number of naturally occurring reactions for a particular cell such as at least 20%, 30%, 50%, 60%, 75%, 90%, 95% or 98% of the total number of naturally occurring reactions that occur in the particular cell.

As used herein, the term "data structure" is intended to mean a physical or logical relationship among data elements, designed to support specific data manipulation functions. The term can include, for example, a list of data elements that can be added combined or otherwise manipulated such as a list of representations for reactions from which reactants can be related in a matrix or network. The term can also include a matrix that correlates data elements from two or more lists of information such as a matrix that correlates reactants to reactions. Information included in the term can represent, for example, a substrate or product of a chemical reaction, a chemical reaction relating one or more substrates to one or more products, a constraint placed on a reaction, a stoichiometric coefficient, or a rate constant.

As used herein, the term "boundary constraint", "reaction constraint" or "flux constraint" is intended to mean an upper or lower bound (or boundary) for a reaction's flux. A bound can specify a minimum or maximum flow of mass, electrons or energy through a reaction. A bound can further specify directionality of a reaction. A bound can be a constant value such as zero, infinity, or a numerical value such as an integer and non-integer. Alternatively, a bound can be a variable value as set forth below. Boundary constraints can be formulated to allow a violation of the bound penalizing bound violations in the objective function. This penalty can be a function of how far the flux value exceeds the bound and can be binary, linear, or quadratic in formulation.

As used herein, the term "variable," when used in reference to a constraint or objective function is intended to mean it is capable of assuming any of a set of values in response to being acted upon by a constraint or objective function. The term "function," when used in the context of a constraint, is intended to be consistent with the meaning of the term as it is understood in the computer and mathematical arts. A function can be binary such that changes correspond to a reaction being off or on. Alternatively, continuous functions can be used such that changes in boundary values correspond to increases or decreases in activity. Such increases or decreases can also be binned or effectively digitized by a function capable of converting sets of values to discreet integer values. A function included in the term can correlate a boundary value with the presence, absence or amount of a biochemical reaction network participant such as a reactant, reaction, enzyme or gene. A function included in the term can correlate a boundary value with an outcome of at least one reaction in a reaction network that includes the reaction that is constrained by the boundary limit. A function included in the term can also correlate a boundary value with an environmental condition such as time, pH, temperature or redox potential.

As used herein, the term "activity," when used in reference to a reaction, is intended to mean the amount of product produced by the reaction, the amount of substrate consumed by the reaction or the rate at which a product is produced or a substrate is consumed. The amount of product produced by the reaction, the amount of substrate consumed by the reaction or the rate at which a product is produced or a substrate is consumed can also be referred to as the flux for the reaction.

As used herein, the term "allosteric regulation" refers to the regulation of a protein or enzyme by a molecule that binds to a site other than the primary active site, thereby altering the activity of the enzyme and the corresponding reaction that it regulates.

As used herein, the term "activate" or activation refers to an effect a compound has on another compound, serving to alter the constraints in a positive manner, such as increasing the activity of a reaction. This includes but is not limited to allosteric and non-allosteric regulation of enzymes.

As used herein, the term "inhibit" or inhibition refers to an effect a compound has on another compound, serving to alter the constraints in a negative manner, such as decreasing the activity of a reaction. This includes but is not limited to allosteric and non-allosteric regulation of enzymes.

As used herein, the term "biomass" refers to a collection of metabolites identified as biomass components, as is common in the art.

As used herein, the term "growth" or "biomass flux" refers to the production of a weighted sum of metabolites identified as biomass components.

As used herein, the term "energy production" refers to the production of metabolites that store energy in their chemical bonds, particularly high energy phosphate bonds such as ATP and GTP.

As used herein, the term "redox equivalent" refers to a metabolite that can alter the oxidation state of other metabolites, generally through the transfer of electrons and or protons. Examples of redox equivalents include $NAD^+$ and $NADP^+$.

As used herein, the term "bioactive small molecule" refers to a metabolite that can inhibit or activate another biological compound, including metabolites, proteins, and nucleic acid polymers.

As used herein, the term "cofactor" refers to a metabolite or chemical compound that is required for a catalytic activity of an enzyme to be carried out.

As used herein, the term "optimization problem" refers to a problem whose solution is obtained through the calculation of a minimum (or maximum) value of the objective function.

As used herein, the term "objective function" refers to a physiological or metabolic function that can be described in terms of the data structure of a network, generally in terms of one or more weighted sum or product of reaction fluxes. This function is either maximized or minimized using optimization algorithms by changing the values of the variables subject to problem constraints.

As used herein, the term "compartment" is intended to mean a subdivided region containing at least one reactant, such that the reactant is separated from at least one other reactant in a second region. A subdivided region included in the term can be correlated with a subdivided region of a cell. Thus, a subdivided region included in the term can be, for example, the intracellular space of a cell; the extracellular space around a cell; the periplasmic space; vacuole or nucleus; or any subcellular space that is separated from another by a membrane or other physical barrier. Subdivided regions can also be made in order to create virtual boundaries in a reaction network that are not correlated with physical barriers. Virtual boundaries can be made for the purpose of segmenting the reactions in a network into different compartments or substructures.

As used herein, the term "substructure" is intended to mean a portion of the information in a data structure that is separated from other information in the data structure such that the portion of information can be separately manipulated or analyzed. The term can include portions subdivided according to a biological function including, for example, information relevant to a particular metabolic pathway such as an internal flux pathway, exchange flux pathway, central metabolic pathway, peripheral metabolic pathway, or secondary metabolic pathway. The term can include portions subdivided according to computational or mathematical principles that allow for a particular type of analysis or manipulation of the data structure.

The reactions included in a reaction network data structure can be obtained from a metabolic reaction database that includes the substrates, products, and stoichiometry of a plurality of biological reactions. The reactants in a reaction network data structure can be designated as either substrates or products of a particular reaction, each with a stoichiometric coefficient assigned to it to describe the chemical conversion taking place in the reaction. Each reaction is also described as occurring in either a reversible or irreversible direction. Reversible reactions can either be represented as one reaction that operates in both the forward and reverse direction or be decomposed into two irreversible reactions, one corresponding to the forward reaction and the other corresponding to the backward reaction.

Reactions included in a reaction network data structure can include intra-system or exchange reactions. Intra-system reactions are the chemically and electrically balanced interconversions of chemical species and transport processes, which serve to replenish or drain the relative amounts of certain metabolites. These intra-system reactions can be classified as either being transformations or translocations. A transformation is a reaction that contains distinct sets of compounds as substrates and products, while a translocation contains reactants located in different compartments. Thus, a reaction that simply transports a metabolite from the extracellular environment to the cytosol, without changing its chemical composition is solely classified as a translocation, while a reaction such as the phosphotransferase system (PTS) which takes extracellular glucose and converts it into cytosolic glucose-6-phosphate is a translocation and a transformation.

Exchange reactions are those which constitute sources and sinks, allowing the passage of metabolites into and out of a compartment or across a hypothetical system boundary. These reactions are included in a model for simulation purposes and represent the metabolic demands placed on a cell. While they may be chemically balanced in certain cases, they are typically not balanced and can often have only a single substrate or product. As a matter of convention the exchange reactions are further classified into demand exchange and input/output exchange reactions.

Input/output exchange reactions are used to allow extracellular reactants to enter or exit the reaction network represented by a model. For each of the extracellular metabolites a corresponding input/output exchange reaction can be created. These reactions can either be irreversible or reversible with the metabolite indicated as a substrate with a stoichiometric coefficient of one and no products produced by the reaction. This particular convention is adopted to allow the reaction to take on a positive flux value (activity level) when the metabolite is being produced or removed from the reaction network and a negative flux value when the metabolite is being consumed or introduced into the reaction network. These reactions will be further constrained during the course of a simulation to specify exactly which metabolites are available to the cell and which can be excreted by the cell.

A demand exchange reaction is always specified as an irreversible reaction containing at least one substrate. These reactions are typically formulated to represent the production of an intracellular metabolite by the metabolic network or the aggregate production of many reactants in balanced ratios such as in the representation of a reaction that leads to biomass formation, also referred to as growth.

A demand exchange reaction can be introduced for any metabolite in a model of the invention. Most commonly these reactions are introduced for metabolites that are required to be produced by the cell for the purposes of creating a new cell such as amino acids, nucleotides, phospholipids, and other biomass constituents, or metabolites that are to be produced for alternative purposes. Once these metabolites are identified, a demand exchange reaction that is irreversible and specifies the metabolite as a substrate with a stoichiometric coefficient of unity can be created. With these specifications, if the reaction is active it leads to the net production of the metabolite by the system meeting potential production demands. Examples of processes that can be represented as a demand exchange reaction in a reaction network data structure and analyzed by the methods of the invention include, for example, production or secretion of an individual protein; production or secretion of an individual metabolite such as an amino acid, vitamin, nucleoside, antibiotic or surfactant; production of ATP for extraneous energy requiring processes such as locomotion; or formation of biomass constituents.

In addition to these demand exchange reactions that are placed on individual metabolites, demand exchange reactions that utilize multiple metabolites in defined stoichiometric ratios can be introduced. These reactions are referred to as aggregate demand exchange reactions. An example of an aggregate demand reaction is a reaction used to simulate the concurrent growth demands or production requirements associated with cell growth that are placed on a cell, for example, by simulating the formation of multiple biomass constituents simultaneously at a particular cellular growth rate.

Depending upon the particular environmental conditions being tested and the desired activity, a reaction network data structure can contain smaller numbers of reactions such as at least 200, 150, 100 or 50 reactions. A reaction network data structure having relatively few reactions can provide the advantage of reducing computation time and resources required to perform a simulation. When desired, a reaction network data structure having a particular subset of reactions can be made or used in which reactions that are not relevant to the particular simulation are omitted. Alternatively, larger numbers of reactions can be included in order to increase the accuracy or molecular detail of the methods of the invention or to suit a particular application. Thus, a reaction network data structure can contain at least 300, 350, 400, 450, 500, 550, 600 or more reactions up to the number of reactions that occur in a particular cell or that are desired to simulate the activity of the full set of reactions occurring in the particular cell.

A reaction network data structure or index of reactions used in the data structure such as that available in a metabolic reaction database, as described herein, can be annotated to include information about a particular reaction. A reaction can be annotated to indicate, for example, assignment of the reaction to a protein, macromolecule or enzyme that performs the reaction, assignment of a gene(s) that codes for the protein, macromolecule or enzyme, the Enzyme Commission (EC) number of the particular metabolic reaction or Gene Ontology (GO) number of the particular metabolic reaction, a subset of reactions to which the reaction belongs, citations to references from which information was obtained, or a level of confidence with which a reaction is believed to occur in a particular cell. A computer readable medium of the invention can include a gene database containing annotated reactions. Such information can be obtained during the course of building a metabolic reaction database or model of the invention as described below.

Flux constraints can be placed on the value of any of the fluxes in a metabolic network. These constraints can be representative of a minimum or maximum allowable flux through a given reaction, possibly resulting from a limited amount of an enzyme present. Additionally, the constraints can determine the direction or reversibility of any of the reactions or transport fluxes in the reaction network data structure.

The ability of a reaction to be actively occurring is dependent on a large number of additional factors beyond just the availability of substrates. These factors, which can be represented as variable constraints in the models and methods of the invention include, for example, the presence of cofactors necessary to stabilize the protein/enzyme, the presence or absence of enzymatic inhibition and activation factors, the active formation of the protein/enzyme through translation of the corresponding mRNA transcript, the transcription of the associated gene(s) or the presence of chemical signals and/or proteins that assist in controlling these processes that ultimately determine whether a chemical reaction is capable of being carried out within an organism.

The methods described herein can be implemented on any conventional host computer system, such as those based on Intel® or AMD® microprocessors and running Microsoft Windows operating systems. Other systems, such as those using the UNIX or LINUX operating system and based on IBM®, DEC® or Motorola® microprocessors are also contemplated. The systems and methods described herein can also be implemented to run on client-server systems and wide-area networks, such as the Internet.

Software to implement a method or model of the invention can be written in any well-known computer language, such as Java, C, C++, Visual Basic, FORTRAN, GAMS, MATLAB or COBOL and compiled using any well-known compatible compiler. The software of the invention normally runs from instructions stored in a memory on a host computer system. A memory or computer readable medium can be a hard disk, floppy disc, compact disc, DVD, magneto-optical disc, Random Access Memory, Read Only Memory or Flash Memory. The memory or computer readable medium used in the invention can be contained within a single computer or distributed in a network. A network can be any of a number of conventional network systems known in the art such as a local area network (LAN) or a wide area network (WAN). Client-server environments, database servers and networks that can be used in the invention are well known in the art. For example, the database server can run on an operating system such as UNIX, running a relational database management system, a World Wide Web application and a World Wide Web server. Other types of memories and computer readable media are also contemplated to function within the scope of the invention.

Data matrices can be represented in a markup language format including, for example, Systems Biology Markup Language (SBML), Hypertext markup language (HTML) or Extensible Markup language (XML). Markup languages can be used to tag the information stored in a database or data structure of the invention, thereby providing convenient annotation and transfer of data between databases and data structures. In particular, an XML format can be useful for structuring the data representation of reactions, reactants and their annotations; for exchanging database contents, for example, over a network or internet; for updating individual elements using the document object model; or for providing differential access to multiple users for different information content of a data base or data structure of the invention. XML programming methods and editors for writing XML code are known in the art as described, for example, in Ray, Learning XML O'Reilly and Associates, Sebastopol, Calif. (2001).

A computer system of the invention can include a user interface capable of receiving a representation of one or more reactions. A user interface of the invention can also be capable of sending at least one command for modifying the data structure, the flux constraints or the commands for applying the constraints to the data representation, or a combination thereof. The interface can be a graphic user interface having graphical means for making selections such as menus or dialog boxes. The interface can be arranged with layered screens accessible by making selections from a main screen. The user interface can provide access to other databases useful in the invention such as a metabolic reaction database or links to other databases having information relevant to the reactions or reactants in the reaction network data structure or to human physiology. Also, the user interface can display a graphical representation of a reaction network or the results of a simulation using a model of the invention.

As used herein, the term "physiological function" is intended to mean an activity of a cell as a whole. An activity included in the term can be the magnitude or rate of a change from an initial state of a cell to a final state of the cell. An activity can be measured qualitatively or quantitatively. An activity included in the term can be, for example, growth, energy production, redox equivalent production, biomass production, compound production, development, flux through a particular reaction or set of reactions, enzyme activity, or consumption of carbon, nitrogen, sulfur, phosphate, hydrogen or oxygen. An activity can also be an output of a particular reaction that is determined or predicted in the context of substantially all of the reactions that affect the particular reaction in a cell or substantially all of the reactions that occur in a cell. Examples of a particular reaction included in the term are production of biomass precursors, production of a protein, production of an amino acid, production of a purine, production of a pyrimidine, production of a lipid, production of a fatty acid, production of a cofactor, production of a bioactive small molecule, flux through a particular reaction or set of reactions, enzyme activity, or transport of a metabolite. The activities or reactions in the physiological function can be increased or decreased. A physiological function can include an emergent property which emerges from the whole but not from the sum of parts where the parts are observed in isolation.

As used herein, the term "metabolic function" refers to flux through a particular or set of reactions, and thereby refers to a type of physiological function.

A physiological function of cellular reactions can be determined using a reaction map to display a flux distribution. A reaction map (network map) can be used to view reaction networks at a variety of levels. In the case of a cellular metabolic reaction network, a reaction map can contain the entire reaction complement representing a global perspective. Alternatively, a reaction map can focus on a particular region of metabolism such as a region corresponding to a reaction subsystem described above or even on an individual pathway or reaction.

Methods disclosed herein can be used to determine the activity of a plurality of cellular reactions including, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite and metabolism of an alternative carbon source.

Methods disclosed herein can be used to determine genetic variations of a cell or organism that enable it to perform a particular physiological function. The physiological function may comprise, for example, biosynthesis of an amino acid, degradation of an amino acid, biosynthesis of a purine, biosynthesis of a pyrimidine, biosynthesis of a lipid, metabolism of a fatty acid, biosynthesis of a cofactor, production of a hormone, production of a bioactive small molecule, transport of a metabolite, metabolism of an alternative carbon source, or biosynthesis of any desired compound the cell is capable of making. The genetic variations can be determined using the methods described above, wherein the reaction network data structure lacks one or more gene-associated reactions. Alternatively, methods can be used to determine genetic variations when a reaction that does not naturally occur in the cell is added to the reaction network data structure. Deletion of a gene can also be represented in a model of the invention by constraining the flux through the associated reaction to zero, thereby allowing the reaction to remain within the data structure. Thus, simulations can be made to predict the effects of adding or removing genes to or from the cell. The methods can be particularly useful for determining the effects of adding or deleting a gene that encodes for a gene product that performs a reaction(s) in a peripheral metabolic pathway. In one contemplated embodiment, vectors are used for in vivo transfer of genes determined in silico to be required for a desired functioning of the metabolic pathway. Other methods are discussed below or known in the art.

The methods of the invention can be used to determine the effects of one or more environmental components or conditions on an activity of a cell. As set forth above, an exchange reaction can be added to a reaction network data structure corresponding to uptake of an environmental component, release of a component to the environment, or other environmental demand. The effect of the environmental component or condition can be further investigated by running simulations with adjusted values for the metabolic flux vector of the exchange reaction target reaction to reflect a finite maximum or minimum flux value corresponding to the effect of the environmental component or condition. The environmental component can be, for example an alternative carbon source or a metabolite that when added to the environment of a cell can be taken up and metabolized. The environmental component can also be a combination of components present for example in a minimal medium composition. Thus, methods disclosed herein can be used to determine an optimal or minimal medium composition that is capable of supporting a particular activity of a cell.

The invention provides methods of generating cells capable of performing a physiological function. Possible genotypes of cells capable of performing a physiological function can first be determined. Cells having the predicted genotypes can then be generated. The cells can be generated by functionally deleting genes or gene products, or increasing or decreasing expression or activity of genes or gene products. In some instances, the cells undergo adaptive evolution to achieve the desired physiological function. Adaptive evolution involves culturing a population of cells for many generations under conditions for which they are not optimally adapted to select for variants with the desired physiological function.

"Functional deletion" or its grammatical equivalents refers to any modification to a cell that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. "Gene" as used herein refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others. In some versions of the invention, "functionally deleted gene product or homolog thereof" means that the gene is mutated to an extent that a gene product or homolog thereof is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, or other variations to a coding sequence or a sequence controlling the transcription or translation of a coding sequence; placing a coding sequence under the control of a less active promoter; blocking transcription of the gene with a trans-acting DNA binding protein such as a TAL effector or CRISPR guided Cas9; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding cell. In certain versions, the genetic modifications giving rise to a functionally deleted gene product are determined with respect to the gene or coding sequence in its unaltered state as found in nature. In certain versions, the genetic modifications giving rise to a functionally deleted gene product are determined with respect to the gene or coding sequence in its form in a corresponding cell.

As used herein, "corresponding cell" refers to a second cell having the same or substantially same genetic and proteomic composition as a first cell, with the exception of genetic and proteomic differences resulting from the modifications described herein for the first cell.

The cells of the invention may be modified to express or increase expression of one or more genes involved in carrying out the physiological function. Modifying a cell to express or increase expression of a gene can be performed using any methods currently known in the art or discovered in the future. Examples include genetically modifying the cell and culturing the cell in the presence of factors that increase expression of the gene. Suitable methods for genetic modification include but are not limited to placing the coding sequence under the control of a more active promoter, increasing the copy number of the gene, and/or introducing a translational enhancer on the gene (see, e.g., Olins et al. *Journal of Biological Chemistry*, 1989, 264(29): 16973-16976). Increasing the copy number of the gene can be performed by introducing additional copies of the gene to the cell, i.e., by incorporating one or more exogenous copies of the native gene or a heterologous homolog thereof into the cellular genome, by introducing such copies to the cell on a plasmid or other vector, or by other means. "Exogenous" used in reference to a genetic element means the genetic element is introduced to a cell by genetic modification. "Heterologous" used in reference to a genetic element means that the genetic element is derived from a different species. A promoter that controls a particular coding sequence is herein described as being "operationally connected" to the coding sequence.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the coding sequences, genes, or gene products described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the coding sequences, genes, or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to coding sequences, genes, or gene products described herein (see below) or those identified by the methods described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

The cells of the invention may include at least one recombinant nucleic acid configured to express or overexpress a particular enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell is one that contains a recombinant nucleic acid molecule or polypeptide. "Overexpress" as used herein means that a particular gene product is produced at a higher level in one cell, such as a recombinant cell, than in a corresponding cell. For example, a cell that includes a recombinant nucleic acid configured to overexpress an enzyme produces the enzyme at a greater amount than a cell that does not include the recombinant nucleic acid.

The cells of the invention may comprise any type of cell. The cells may be isolated, dispersed, or in the form of an organ or tissue. Exemplary cells comprise microorganisms. The microorganisms may be prokaryotic or eukaryotic. Suitable prokaryotes include bacteria and archaea. Suitable types of bacteria include gram-positive bacteria, gram-negative bacteria, ungrouped bacteria, phototrophs, lithotrophs, and organotrophs. Suitable eukaryotes include yeast and other fungi.

The invention also provides methods for increasing or decreasing compound production or increasing or decreasing select enzyme activities with the cells of the present invention. The methods involve culturing the microorganism in conditions suitable for growth of the cell. In some instances, the cells undergo adaptive evolution to achieve the desired physiological function. The cell either directly produces the desired compound or produces precursors from which the desired compound is spontaneously converted. The desired compound may be any metabolite the cell naturally generates or any metabolite the cell does not naturally generate but is capable of generating through genetic modification.

The select enzyme activity may be the activity of an enzyme naturally encoded in the organism's genome or may be an enzyme that is heterologously expressed. Conditions for culturing cells are well-known in the art. Such conditions include providing suitable carbon sources for the particular cell along with suitable micronutrients. For eukaryotic cells and heterotrophic bacteria, suitable carbon sources include various carbohydrates. Such carbohydrates may include biomass or other suitable carbon sources known in the art. For phototrophic bacteria, suitable carbon sources include $CO_2$, which is provided together with light energy.

Methods of producing a desired compound with the cells of the present invention may also include isolating the desired compound from the cell. Methods of isolating various compounds from cells are well-known in the art.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

The following examples are intended to illustrate but not limit the invention.

EXAMPLES

Introduction to Examples

Computational modelling of cells has enabled both qualitative and quantitative descriptions and predictions of cellular behavior. In particular, constraint-based modelling methods utilizing genome-scale metabolic models have been widely used to predict cellular fluxes. Flux Balance Analysis (FBA)—which predicts the flux distribution in a cell—is the most fundamental of these methods and has been in use for over twenty years (Orth 2010). FBA has been utilized in drug discovery (Kim 2012), biofuel production (Liu 2012), and other biotechnology applications. FBA has been extended to predict cellular perturbations for flux coupling (Burgard 2004), predictions of non-steady state behavior (Segrè 2002, Shlomi 2005, Kim 2012), incorporation of regulatory networks (Covert 2008), the incorporation of expression data (Machado 2014), and numerous other applications. FBA assumes that the reaction rates in a cell are chosen to maximize an objective function, such as cellular growth. FBA quickly calculates cellular states and its predictions have been found to be consistent with experiments under a wide variety of conditions for evolved cells.

FBA can make inaccurate flux predictions when cells have not evolved to maximize growth or where other processes (e.g., regulation) limit metabolic fluxes. For example, when cells are perturbed from their optimal wild type state, by changing media conditions or removing genes, they often do not exhibit maximum growth. Instead, a variety of perturbation methods (Segrè 2002, Shlomi 2005, Kim 2012) have been developed which predict fluxes that are close to the un-perturbed wild-type flux distribution. Of particular note, the minimization of metabolic adjustments (MOMA) minimizes the squared difference between fluxes in a knockout strain and the wild-type strain (Segrè 2002). These methods are more accurate for perturbed states than FBA; however, adaptive evolution of the perturbed strain may eventually lead to flux distributions more similar to those predicted by FBA.

Measurements of sugar and oxygen uptake rates or by-product (e.g., acetate, lactate, $CO_2$) production can easily be incorporated into constraint-based models to further constrain the FBA problem to better predict the observed phenotype. Unfortunately, many different intracellular flux distributions could be consistent with these measurements (Kim 2012, Mahadevan 2003). In order to further constrain the predicted flux distribution, intracellular fluxes can be measured using $^{13}C$ metabolic flux analysis (MFA) (Zamboni 2009). While MFA estimates intracellular fluxes with high precision, the experiments are more difficult and costly to perform than experiments measuring extracellular fluxes. As a result, MFA has been applied to a relatively few number of organisms. Therefore, in situations where we desire high quality descriptive modelling data, it is unlikely that MFA data is available.

Other approaches for improving flux predictions have used expression data, proteomics data, or transcriptional regulatory models to restrict fluxes through parts of the metabolic network. However, a recent study of existing expression-based methods showed existing approaches make worse predictions than FBA (Machado 2014). Outside of transcriptomic and proteomic data, metabolomics data cannot be incorporated directly without considering thermodynamic and kinetic information. These methods again require extensive knowledge of the organism and the kinetics of the particular enzymes in vivo, something that is unlikely to be available for most organisms.

Figure 2:
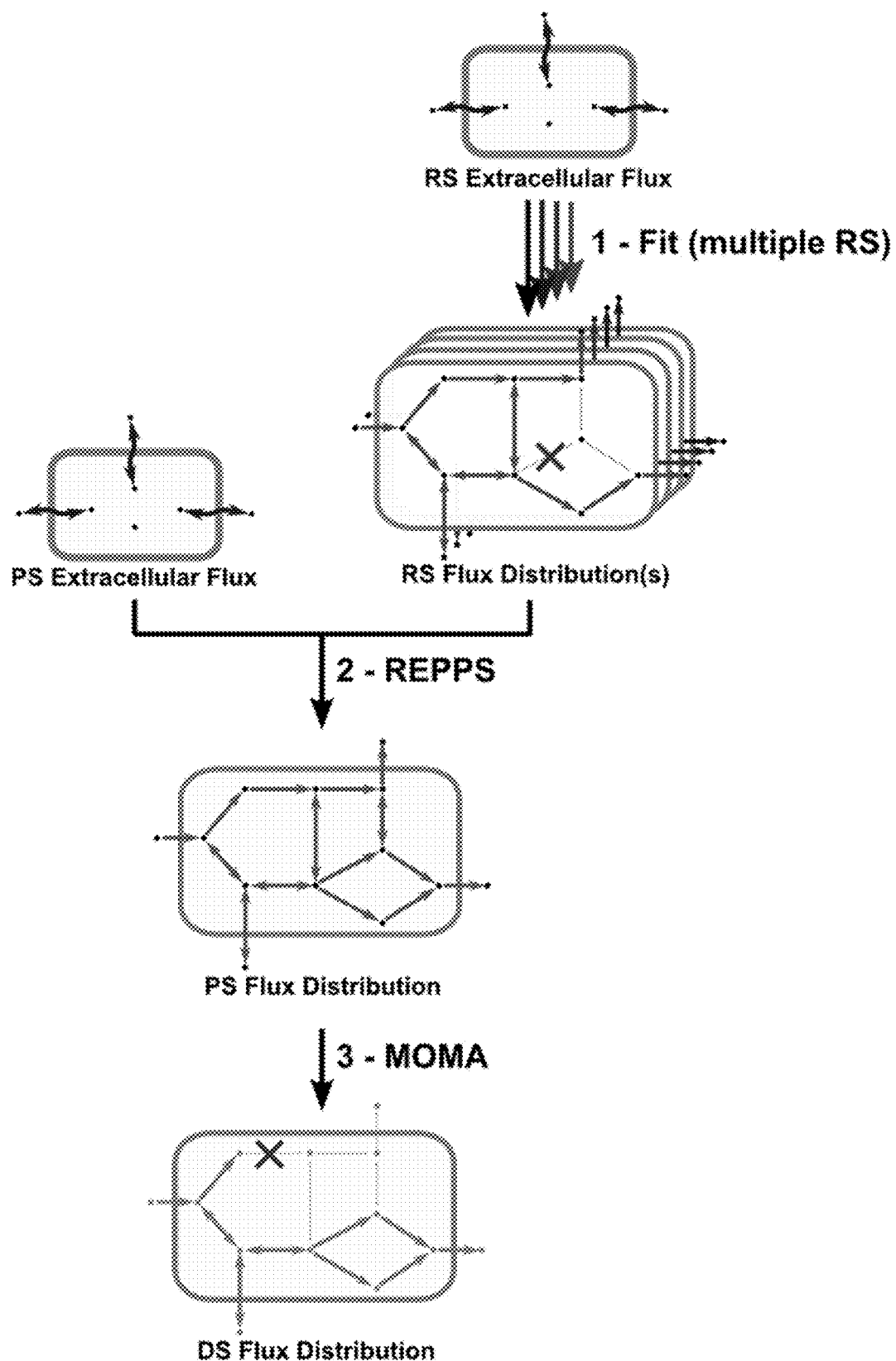
FIG. 2 is a schema depicting a method of the present invention for determining flux distribution of a parental strain (PS) and derived strains (DS) therefrom. The method replaces the parental strain's gene expression and MFA data with extracellular flux data from multiple reference strains (RS). Each reference strain has its flux distribution calculated independently and these estimations are combined with extracellular flux data from the parental strain to estimate the parental strain flux distribution. After calculating the parental strain flux distribution, new derived strains can be estimated using existing methods.

In the following Examples, we propose and evaluate variations of a novel method which incorporates easily measured extracellular fluxes for a parental strain and multiple perturbed reference strains (e.g. knockouts). This method, referred to herein as RElative Phenotypes for Parental Strain estimation (REPPS), considers the available data for the parental and perturbed reference strains to describe the intracellular flux distributions in the parental strain. Using this method, we are able to better predict the intracellular flux distribution for the parental strain. FIGS. 1 and 2 show this process in detail in comparison to RELATCH. RELATCH utilizes measured extracellular fluxes, MFA data, and gene expression data to first estimate fluxes and enzyme contributions in the parental strain and then predicts fluxes in derived strains, such as gene knockouts. REPPS similarly uses experimental data to improve the parental strain flux estimation, which helps improve flux predictions of subsequently derived strains. Unlike RELATCH, REPPS does not require expression or MFA data. Instead, REPPS utilizes extracellular flux data from multiple reference strains and the parental strain. These reference strains are functionally equivalent to the derived strains, in that they are all related to the parental strain (e.g. the reference strains and derived strains are single gene knockouts of a parental strain). Data from the reference strains are used to estimate fluxes in the parental strains, and these flux estimates are subsequently used to predict fluxes in the derived strains. By utilizing only a small number of reference strains, we can greatly improve the accuracy of the parental strain flux estimation and thus improve the prediction of derived-strain phenotypes. Improving flux estimations can reduce the number of experiments necessary to create a desired production strain, and thus can improve the ability to engineer strains in novel organisms.

Example 1 provides an example of REPPS using extracellular flux data in addition to gene expression data. Example 2 provides an example of REPPS using extracellular flux data without gene expression data.

Example 1

1.1 Materials and Methods 1.1.1 Experimental Data, Genome Scale Metabolic Models, and Constraint-Based Methods Experimental data for both the wild-type and knockout mutants of *Escherichia coli* K-12 were obtained from the Keio University *E. coli* multi-omics database of in-frame single-gene deletion strains (Ishii et al. 2007). This dataset includes $^{13}C$ metabolic flux analysis (MFA), extracellular flux, and gene expression data which were used in this study. All MFA fluxes were reported as a percentage of the glucose substrate uptake. In order to convert these values to actual fluxes, they were multiplied by the glucose consumption rate which was measured separately and reported as mmol/g-dry weight (gDW) of biomass/hour. All mRNA expression data was reported as copy number/μg-total RNA. The genome-scale metabolic model of *E. coli*, iJR904 (Reed et al. 2003) was used in this study.

Fluxes in reference strains (i.e., mutant flux distributions, denoted by $u_{j,r}$, used to estimate the parental flux distribution) were calculated using either parsimonious flux balance analysis (pFBA) (Lewis et al. 2010) or with a modified RELATCH Fit equation which are described below (see 1.1.5 and 1.1.2 for details). pFBA predictions were computed by constraining the growth rate to the measured value and fitting the measured extracellular fluxes before minimizing the total flux usage. Parental strain flux distributions were estimated using either pFBA (see 1.1.5 for details, Lewis et al. 2010), modified RELATCH Fit (see 1.1.2 for details), or REPPS (see 1.1.3 for details). For REPPS, flux estimates for a set of reference strains (referred to as the reference set, R) were used to estimate the parental strain fluxes ($w_j$). Additional flux distributions for derived strains ($v_j$) that are not part of the reference strain set were predicted—using the parental strain as a starting point—using either RELATCH (Kim et al. 2012) or MOMA (Segrè et al. 2002) as described in section 1.1.5. These derived strain's flux distributions were also calculated using pFBA (Lewis et al. 2010) and the modified RELATCH Fit (see 1.1.2 for details) for comparison.

All optimization problems were solved using CPLEX (for pFBA), CONOPT (for RELATCH Fit, MOMA, RELATCH, and REPPS), or IPOPT (for flux variability analysis) accessed using GAMS 24.1.3 (GAMS Development Corp.; 1217 Potomac St, NW; Washington D.C. 20007, USA).

1.1.2 Estimating the Reference Flux Distributions Using RELATCH Fit

The flux distribution ($u_j$) and enzyme contribution ($U_j^{enz}$) for each reference strain within a training set of reference strains (R) were first estimated. This requires the problem (Eqs. 1a-1g) to be solved repeatedly for each reference strain (r) within R.

In order to calculate these values without MFA data, the RELATCH fit function (Kim et al. 2012) was slightly modified to use only experimentally measured fluxes ($u^{ex}$) within the set of measured extracellular fluxes ($J_{ex}$), as well as gene expression data (E). The flux data is incorporated into the first term of the objective function variable ($\gamma_r$) (Eq. 1g), where the sum-squared difference between the experimentally measured and estimated fluxes. The second term weights enzyme contributions for enzymes by their expression levels. These enzyme contributions are non-negative (Eq. 1e) and indicate how much flux each isozyme can contribute towards total flux through a reaction. The enzyme contribution is only used for reactions with a gene to protein to reaction associations ($J^{GPR}$) and have known associated enzymes (N(j)). The enzyme contributions, when summed across isozymes, are the maximum capacity of enzymes to catalyze a reaction in either direction (Eq. 1d). Steady-state mass balance and reaction irreversibility ($J^{irr}$ contains only reactions which are irreversible) constraints are also enforced (Eq. 1b-c). While the reference strains are not necessarily limited to knockout strains, in this study we performed analysis solely using knockout strains as the reference stains. Therefore, for each mutant in the reference set R, we added constraints to remove enzyme contributions for genes which have been knocked out ($G_{KO}$) (Eq. 1f). The sets $J_{irr}$ and $J^{ex}$ are subsets of the set of all reactions J.

$$\min_{u,U^{enz}} \gamma_r \ \forall \ r \in R \tag{1a}$$

$$\text{S.T} \sum_{j \in J} S_{i,j} \cdot u_{j,r} = 0 \ \forall \ i \in I \tag{1b}$$

$$u_{j,r} \geq 0 \ \forall \ j \in J^{irr} \tag{1c}$$

$$-\sum_{n \in N(j)} U_{j,n,r}^{enz} \leq u_{j,r} \leq \sum_{n \in N(j)} U_{j,n,r}^{enz} \ \forall \ j \in J^{GPR} \tag{1d}$$

$$U_{j,n,r}^{enz} \geq 0 \ \forall \ j \in J, \forall \ n \in N(j) \tag{1e}$$

$$U_{j,n,r}^{enz} = 0 \ \forall \ \{j \in J^{GPR}(g), n \in N(j, g) \mid g \in G_r^{KO}\} \tag{1f}$$

$$\gamma_r = \sum_{j \in J^{ex}} (u_{j,r} - u_{j,r}^{ex})^2 + \sum_{j \in J^{GPR}} \sum_{n \in N(j)} \frac{(U_{j,n,r}^{enz})^2}{E_{j,n,r}} \ \forall \ j \in J^{GPR} \tag{1g}$$

1.1.3 Predicting the Parental Flux Distribution Using REPPS

Once the reference strain's flux distributions and corresponding enzyme contributions for all the mutants in the reference set R have been calculated, we then proceeded to use REPPS to calculate the parental strain flux distribution (w) and enzyme contributions ($W^{enz}$).

While all flux estimates for the reference strains (in R) can be used, there may be differences in the quality of fit between experimental measurements and model predictions (measured as $\gamma_r$ for strain r) across the different reference strains. In the reference flux distribution estimation (Eq. 1), the objective value ($\gamma_r$) is a measure of the difficulty of fitting the flux distribution to the experimentally measured data. Therefore, a weighting factor ($f_r$) is defined which will vary linearly from 0.5 to 1.5 depending upon the quality of the fit, with a larger weighting factor corresponding to a better fit (Eq. 2).

$$f_r = 1.5 - \frac{\gamma_r - \min(\gamma_r \mid r \in R)}{\max(\gamma_r \mid r \in R) - \min(\gamma_r \mid r \in R)} \ \forall \ r \in R \tag{2}$$

REPPS also uses relative differences between the gene expression data for the parental strain ($E_g^{PS}$) and each reference strain ($E_{g,r}$) for every measured gene ($G^{ge}$). The direction of the gene expression difference is stored as a directional parameter (d) (Eq. 3).

$$d_{g,r} = \begin{cases} 1 & E_g^{PS} > E_{g,r} \\ 0 & E_g^{PS} = E_{g,r} \\ -1 & E_g^{PS} < E_{g,r} \end{cases} \ \forall \ g \in G^{ge}, \forall \ r \in R \tag{3}$$

Once these directional parameters have been defined, it is then possible to solve REPPS (Eq. 4) for the parental flux distribution and enzyme contributions. The objective function for REPPS contains three terms (Eq. 4a) which can be weighted by selecting α, β, and δ to adjust their relative contributions to the objective function. The first term ($c^{ex}$) represents the sum-squared difference between the experimentally measured ($w^{ex}$) and estimated fluxes (Eq. 40 normalized by the number of measured fluxes. The second term ($c^{rs}$) measures the sum-squared distance between the parental and reference strains' fluxes, with the difference being scaled by a weighting factor ($f_r$, indicating the quality of each reference strain's fit, Eq. 2), the number of reference strains, and the number of estimated parental fluxes (Eq. 4g). Finally, the third term ($c^{ge}$)—in combination with constraints 4i-j—quantifies violations (e) of the enzyme contributions' bounds defined by gene expression differences (Eq. 4h), which are scaled by the fit quality factor ($f_r$) and normalized by the number of genes with measured expression and number of reference strains. If the change in enzyme contribution between the parental and a reference strain has an opposite sign to the change in gene expression data for the respective strains, then the enzyme contribution directional violation term ($e_{g,r}$) becomes positive (Eq. 4i) and is penalized in the objective function (Eq. 4a). If, however, the expression and enzyme contribution change is in the same direction then $e_{g,r}$ can be zero (Eq. 4i). The remaining constraints (Eq. 4b-e) are analogous to those described in section 1.1.2 (Eq. 1b-e) except the parental strain fluxes (w) and enzyme contributions ($W^{enz}$) are used.

$$\min_{w, W^{enz}, s} \alpha \cdot c^{ex} + \beta \cdot c^{rs} + \delta \cdot c^{ge} \quad (4a)$$

$$\text{S.T} \sum_{j \in J} S_{i,j} \cdot w_j = 0 \quad \forall i \in I \quad (4b)$$

$$w_j \geq 0 \quad \forall j \in J^{irr} \quad (4c)$$

$$-\sum_{n \in N(j)} W_{j,n}^{enz} \leq w_j \leq \sum_{n \in N(j)} W_{j,n}^{enz} \quad \forall j \in J^{GPR} \quad (4d)$$

$$W_{j,n}^{enz} \geq 0 \quad \forall j \in J^{GPR}, \forall n \in N(j) \quad (4e)$$

$$c^{ex} = \frac{1}{\|J^{ex}\|} \sum_{j \in J^{ex}} (w_j - w_j^{ex})^2 \quad (4f)$$

$$c^{rs} = \frac{1}{\|R\| \cdot \|J\|} \sum_{r \in R} \sum_{j \in J} f_r \cdot (w_j - u_{j,r})^2 \quad (4g)$$

$$c^{ge} = \frac{1}{\|R\| \cdot \|G^{ge}\|} \sum_{r \in R} \sum_{g \in G^{ge}} f_r \cdot (e_{g,r})^2 \quad (4h)$$

$$e_{g,r} \geq d_{g,r} \cdot \sum_{j \in J^{GPR}} \sum_{n \in N(g)} (U_{j,n,r}^{enz} - W_{j,n}^{enz}) \quad (4i)$$
$$\forall g \in G^{ge}, \forall r \in R$$

$$e_{g,r} \geq 0 \quad \forall r \in R \quad (4j)$$

1.1.4 Error Calculation and Plotting

For the majority of these analyses, the mean sum-squared error (MSE) was used as a measure of the accuracy of the flux predictions. This was defined as the sum of the squared difference between the experimentally measured MFA data ($w^{MFA}$) (Ishii et al. 2007) and the computationally predicted flux (w) divided by the number of fluxes being compared (Eq. 5). These predicted fluxes could be for parental strain that were calculated using pFBA (see 1.1.5 for details), RELATCH Fit (see 1.1.2 for details, using parental strain instead of reference strain experimental data), or REPPS; or for knockout mutants (where w is replaced with v) that were calculated using RELATCH or MOMA (see 1.1.5 for details). For the parental strain, the expression, extracellular flux, and MFA data from experiment RF05 was used.

$$MSE = \frac{1}{\|J^{MFA}\|} \cdot \sum_{j \in J^{MFA}} (w_j^{MFA} - w_j)^2 \quad (5)$$

All plots were made using R version 3.1 (R Foundation for Statistical Computing, 2013) and the 'gdxrrw' package version 0.3.1 for importing data between GAMS and R.

1.1.5 Flux Predictions Using pFBA, MOMA, and RELATCH pFBA (Lewis et al. 2010) was used to calculate fluxes in the parental strain for comparison to REPPS. pFBA minimizes the absolute value of the total fluxes (Eq. 6a). This problem was further constrained by the set of experimentally measured fluxes (Eq. 6d). The experimentally measured flux values were first adjusted by minimizing the Euclidean distance between their measured values and the predicted values of the experimentally measured fluxes that are consistent with mass balance (Eq. 6b) and reaction irreversibility constraints (Eq. 6c) at the experimental growth rate. Once the optimal experimentally measured flux values ($w_j^{ex}$) were found they were used to find a flux distribution (w) that was consistent with these values and which minimized the absolute value of the total fluxes (Eq. 6). The resulting flux distribution is a pFBA solution. Since alternate equivalent solutions exist to the pFBA problem, we found the pFBA solution that further maximized the MSE (see section 1.4) to represent the worst case scenario.

$$\min_w \sum_{j \in J} |w_j| \quad (6a)$$

$$\text{S.T.} \sum_{j \in J} S_{i,j} \cdot w_j = 0 \quad \forall i \in I \quad (6b)$$

$$w_j \geq 0 \quad \forall j \in J^{irr} \quad (6c)$$

$$w_j = w_j^{ex} \quad \forall j \in J^{ex} \quad (6d)$$

Fluxes in derived strains that were not part of the reference set R were calculated using either MOMA (Segre et al. 2002) or RELATCH (Kim et al. 2012). MOMA (Eq. 7) was used to calculate the flux distribution in a derived strain (v) by minimizing the Euclidian distance between the derived strain's flux distribution and a previously estimated parental strain's flux distribution (Eq. 7a). As before, steady-state mass balance (Eq. 7b) and irreversible reaction constraints are enforced (Eq. 7c). Finally, MOMA constrains fluxes to be zero that depend on the knocked out gene(s) (Eq. 7d). For this study, fluxes were only constrained to be zero if all isozymes for a particular reaction were deleted.

$$\min_v \sum_{j \in J} (w_j - v_j)^2 \quad (7a)$$

$$\text{S.T.} \sum_{j \in J} S_{i,j} \cdot v_j = 0 \quad \forall i \in I \quad (7b)$$

$$v_j \geq 0 \quad \forall j \in J^{irr} \quad (7c)$$

$$v_j = 0 \quad \forall \{j \in J(g) \mid g \in G^{KO}\} \quad (7d)$$

RELATCH (Kim et al. 2012) was also used to calculate flux distributions in derived strains that were not part of the reference set R. RELATCH differs from MOMA in several significant ways. First, RELATCH treats reactions (and enzyme contributions) that were active in the parental strain differently in the objective function from those which were not active. For previously active (i.e., non-zero) reactions, RELATCH uses a relative distance in its objective function, where the relative distance between the knockout and parental strain flux distribution (normalized by the parental strain's flux values), as compared to the absolute distance used in MOMA (Eq 7a). For previously inactive reactions, the enzyme contributions which were zero in the parental strain and can be 'turned on' in the derived strains using a second term in the objective function. This penalizes using a new pathway and the additional enzymes which must be produced to do so. For further detail on RELATCH, see Kim et al. 2012.

1.2 Results
1.2.1 Predicting the Parental Flux Distribution Using REPPS

Parental strain flux distributions were calculated using REPPS (Eq. 1 and Eq. 4) and compared to parental strain flux distributions calculated using pFBA (Eq. 6) or RELATCH Fit (Eq. 1, where data for the parental strain is used instead of the reference strains). Predictions were made using a genome-scale metabolic model of *E. coli*, iJR904. The results are shown in Table 1. All these calculations were done using a randomly chosen set of reference strains containing five mutants from the Keio dataset (Δgnd, Δrpe, ΔrpiA, ΔtktA, ΔtalA).

TABLE 1

Comparison of REPPS, pFBA, and RELATCH Fit in Predicting Parental Flux Distribution in the iJR904 Genome-Scale Metabolic Model of *E. coli*.

| Parental Strain Method | MSE* using iJR904 |
|---|---|
| pFBA | 1.248 |
| RELATCH Fit | 1.833 |
| REPPS | 0.701 |

*MSE in units of $(mmol/gDW/h)^2$

Figure 3:
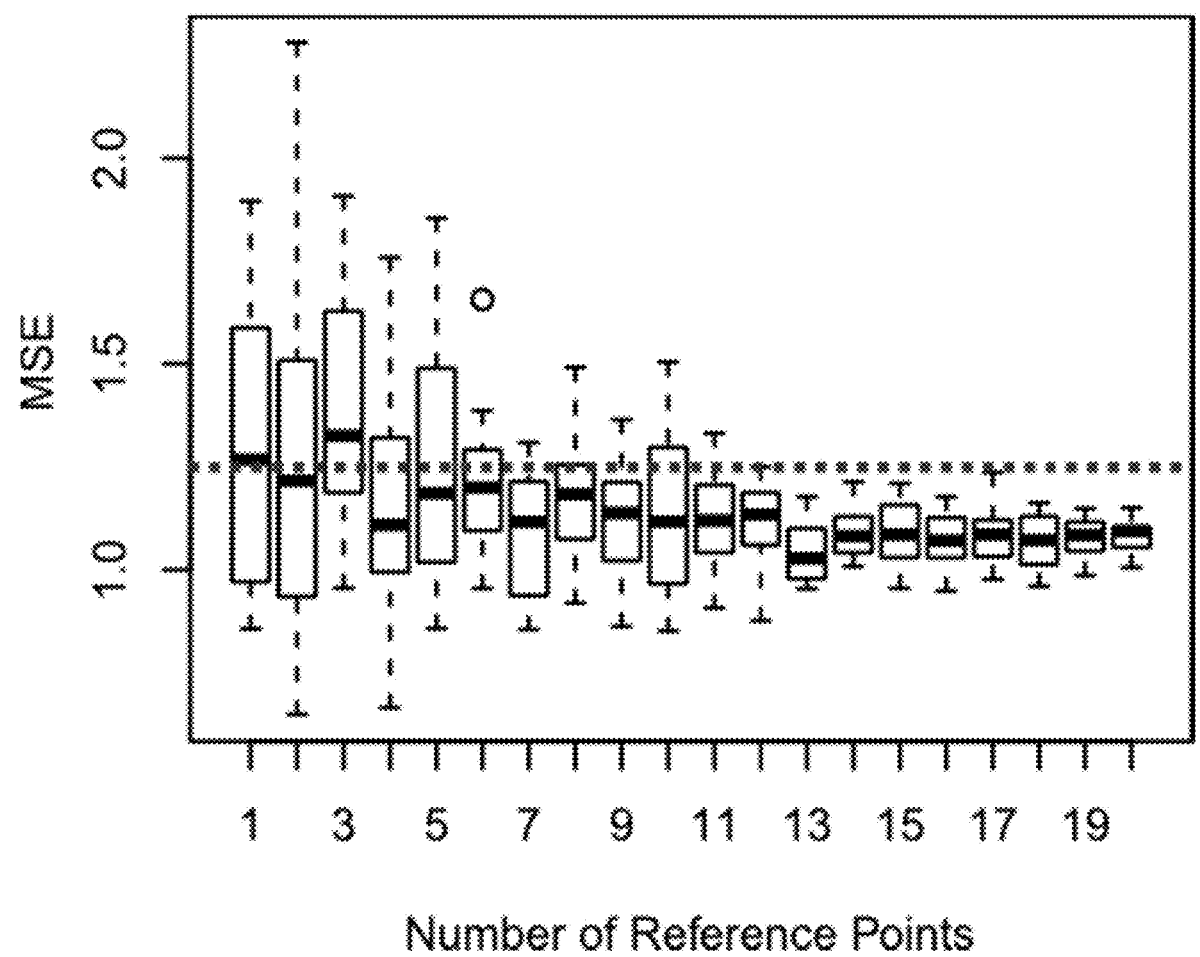
FIG. 3 shows the effect of the number of reference points (number of analyzed knockout reference strains) on error (mean squared error between estimated and measured flux values) for iJR904. The *Escherichia coli* (*E. coli*) genome-scale metabolic model was used with the methods of the present invention (REPPS) to determine the parental strain flux distribution in the absence of metabolic flux analysis data. The error for the corresponding pFBA (an existing method) solution for the parental strain is shown as a dotted horizontal line.

REPPS yielded a lower MSE (in $[mmol/gDW/h]^2$) than pFBA and RELATCH Fit, indicating that REPPS predicts the parental flux distribution better than FBA and RELATCH Fit. We subsequently evaluated how REPPS performed using different randomly chosen sets of reference strains with different numbers of strains included in R (i.e., by varying $\|R\|$). Results for the MSE versus the size of the reference set (i.e., number of reference strains) for iJR904 are shown in FIG. 3. These results show that a relatively small number of reference strains are needed for REPPS to improve flux predictions over pFBA.

1.2.2 Flux Predictions for Derived Strains

Figure 4:
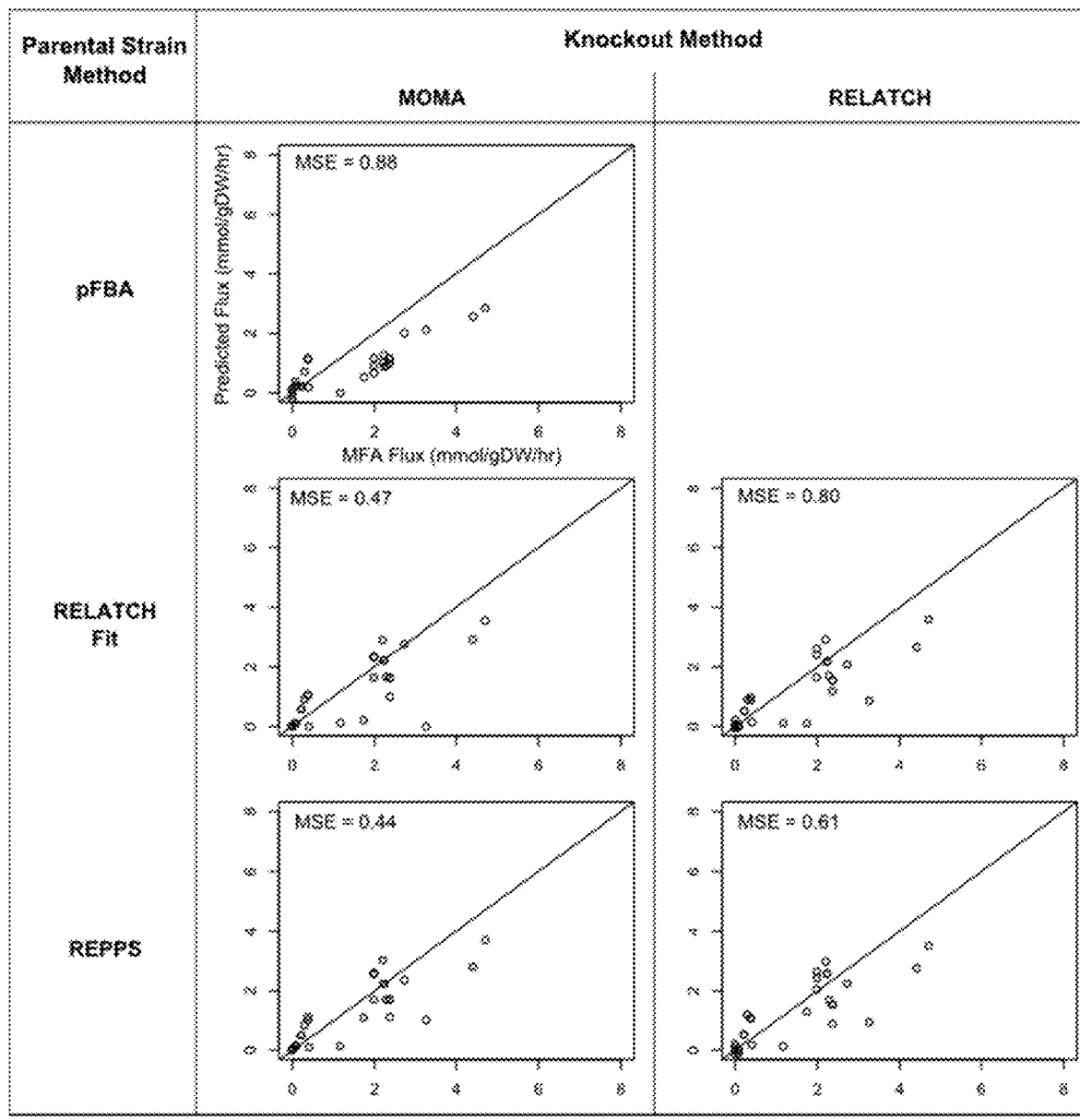
FIG. 4 shows the measured fluxes using MFA versus predicted fluxes for a single knockout strain (ΔpfkA) using the iJR904 *E. coli* genome-scale metabolic model with FBA, RELATCH Fit, or REPPS to calculate the parental strain flux distribution and either MOMA or RELATCH to predict the derived strain (a knockout of the parent strain) flux distribution. The diagonal line indicates a perfect 1:1 correlation between the predicted and measured fluxes.
Figure 5:
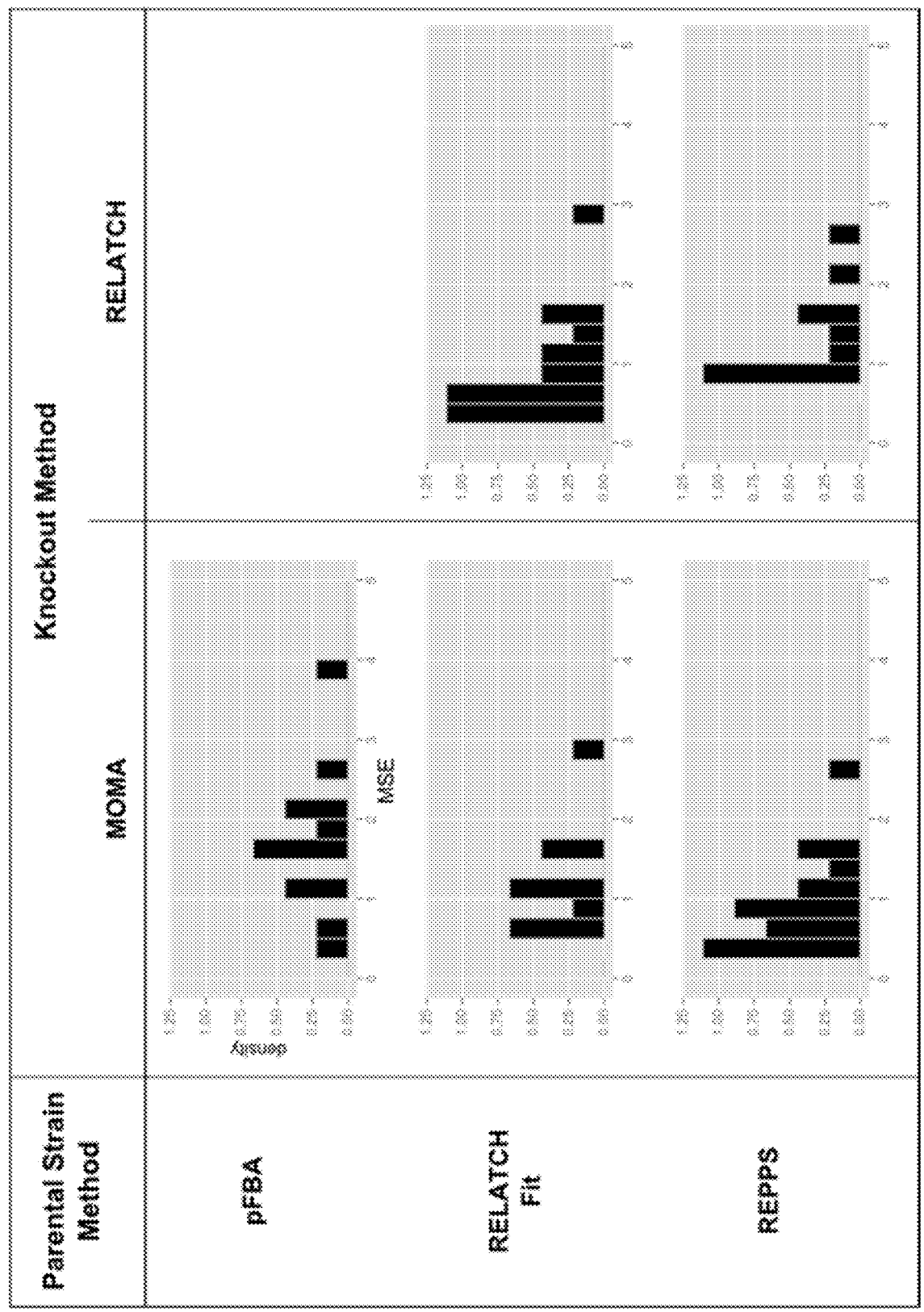
FIG. 5 shows the distribution of mean squared errors (MSE) in the predicted flux values for derived strains (knockouts of the parental strain) using iJR904 *E. coli* genome-scale metabolic model and FBA, RELATCH Fit, or REPPS (the current invention) to calculate the parental strain flux distribution and either MOMA or RELATCH to predict the derived strain flux distribution. The derived strains shown in the figure were all knockouts which were not included in the reference strain set.

Parental strain flux distributions can be predicted using pFBA, RELATCH Fit, and REPPS and these predictions can be used to make predictions for new derived strains. The previous section showed that REPPS predictions were closest to flux measurements obtained by $^{13}C$ MFA for the parental strain. We next investigated how different parental strain flux distributions (calculated using pFBA, RELATCH Fit, and REPPS) affected predictions for derived strains that were not included as reference strains for REPPS parental strain flux estimates. The iJR904 genome-scale model was used as before. For derived strains flux predictions MOMA or RELATCH was used with each of the different predicted parental strain flux distributions (estimated using pFBA, RELATCH Fit, or REPPS). Using REPPS to predict the parental strain flux distribution and enzyme contributions resulted in lower MSEs than using pFBA or RELATCH Fit, regardless of the method (RELATCH or MOMA) used to predict the knockout strain flux distribution. See FIGS. 4 and 5.

Example 2

2.1 Materials and Methods
2.1.1 Genome Scale Metabolic Models

All *Escherichia coli* modelling was performed using the iJR904 model (Reed 2003), as in Example 1. Experimental data for both the parental strain and knockout mutants of *Escherichia coli* K-12 were obtained from the Keio University *E. coli* multi-omics database of in-frame single-gene deletion strains (Ishii et al. 2007), as in Example 1. We utilized $^{13}C$ metabolic flux analysis (MFA) and extracellular flux data. All MFA fluxes were reported as a percentage of the glucose substrate uptake. In order to convert these values to actual fluxes, the reported MFA fluxes were multiplied by the reported glucose consumption rate. For the parental strain flux distribution, the data from three replicate experiments (RF03, RF05, and RF06) were averaged together to represent the mean MFA and extracellular flux values for the parental strain.

As in Example 1, all optimization problems were solved using CPLEX (for pFBA), CONOPT (for RELATCH Fit, MOMA, RELATCH, and REPPS), or IPOPT (for flux variability analysis) accessed using GAMS 24.1.3 (GAMS Development Corp.; 1217 Potomac St, NW; Washington D.C. 20007, USA).

All plots were made using R version 3.1 (R Foundation for Statistical Computing, 2013) and the 'gdxrrw' package version 0.3.1 for importing data between GAMS and R.

2.1.2 Estimating Reference Strain Flux Distribution

Fluxes in the reference strains were estimated using either pFBA (Lewis 2010) or a modified form of the RELATCH Fit function (Reed 2012), which will be referred to as the "Fit" method.

pFBA required two steps. The first was to minimize the difference between the experimentally measured extracellular fluxes ($u_j^{ex}$) and estimated extracellular fluxes (up for the given reference strain. Fluxes associated with genes that were knocked out were forced to be zero using equation 8d.

$$\min_{u_j^r} \sum_{j \in J^{ex}} (u_j^r - u_{j,r}^{ex})^2 \quad (8a)$$

$$\text{S.T.} \sum_{i \in I} S_{i,j} \cdot u_j^r = 0 \quad \forall j \in J \quad (8b)$$

$$u_j^r \geq 0 \quad \forall j \in J^{irr} \quad (8c)$$

$$u_j^r = 0 \quad \forall j \in J_{KO} \quad (8d)$$

After the best fit of the extracellular flux data is performed, the corresponding extracellular fluxes are fixed and the sum of the absolute value of all fluxes ($u_{j,r}$) is then minimized.

$$\min_u \sum_{j \in J} |u_{j,r}| \quad (9a)$$

$$\text{S.T.} \sum_{i \in I} S_{i,j} \cdot u_{j,r} = 0 \quad \forall j \in J \quad (9b)$$

$$u_{j,r} \geq 0 \quad \forall j \in J^{irr} \quad (9c)$$

$$u_{j,r} = u_j^r \quad \forall j \in J^{ex} \quad (9d)$$

$$u_{j,r} = 0 \quad \forall j \in J_{KO} \quad (9e)$$

The Fit method combines these two steps into one process and instead of minimizing the sum of absolute fluxes, minimizes the enzymatic contribution ($U_{j,n,r}^{enz}$) to reactions. The enzymatic contribution term is a proxy for the amount of enzyme required for all of the reactions that it catalyzes. It is explained in more detail in (Kim et al. 2012).

$$\min_{u, U^{enz}} \sum_{j \in J^{ex}} (u_{j,r} - u_{j,r}^{ex})^2 + \gamma \sum_{j \in J_{GPR}} \sum_{n \in N(j)} U_{j,n,r}^{enz} \quad (10a)$$

-continued $$\text{S.T.} \sum_{i \in I} S_{i,j} \cdot u_{j,r} = 0 \quad \forall j \in J \tag{10b}$$

$$u_{j,r} \geq 0 \quad \forall j \in J^{irr} \tag{10c}$$

$$-\sum_{n \in N(j)} U_{j,n,r}^{enz} \leq u_{j,r} \leq \sum_{n \in N(j)} U_{j,n,r}^{enz} \quad \forall j \in J_{GPR} \tag{10d}$$

$$U_{j,n,r}^{enz} \geq 0 \quad \forall j \in J_{GPR}, n \in N(j) \tag{10e}$$

$$U_{j,n,r}^{enz} = 0 \quad \forall j \in J_{KO}, n \in N(j) \tag{10f}$$

Regardless of the method used, each method was applied to multiple reference strains, with the resulting fluxes for reaction j in strain r denoted as $u_{j,r}$.

2.1.3 Determining Parental Strain Flux Distribution with REPPS

REPPS is used to calculate the parental strain flux distribution. It utilizes two terms (Eq. 11). The first is analogous to the extracellular flux fitting found in the reference strain methods (section 2.1.2) but is performed on the parental strain fluxes ($w_j$). The first term thus minimizes the distance between experimentally measured fluxes and estimated fluxes of the parental strain and is normalized by the number of extracellular fluxes measured. The second term minimizes the distance between the flux estimations in the reference strains and the flux estimations of the parental strain and is normalized by the number of reference strains and the number of total reactions.

$$\min_{w, W^{enz}} \frac{\sum_{j \in J_{ex}} (w_j - w_j^{ex})^2}{\|J^{ex}\|} + \beta \frac{\sum_{r \in R} \sum_{j \in J} (w_j - u_{j,r})^2}{\|R\| \cdot \|J\|} \tag{11a}$$

$$\text{S.T.} \sum_{i \in I} S_{i,j} \cdot w_j = 0 \quad \forall j \in J \tag{11b}$$

$$w_j \geq 0 \quad \forall j \in J^{irr} \tag{11c}$$

$$-\sum_{n \in N(j)} W_{j,n}^{enz} \leq w_j \leq \sum_{n \in N(j)} W_{j,n}^{enz} \quad \forall j \in J_{GPR} \tag{11d}$$

$$W_{j,n}^{enz} \geq 0 \quad \forall j \in J_{GPR}, n \in N(j) \tag{11e}$$

Equation 11 is based on Equation 4 in Example 1 wherein δ=0 and α=1. This negates the relevance of the enzyme contribution term in Equation 4a and results in Equations 4h, 4i, and 4j being non-binding. The removal of these constraints further removes the dependency of this formulation on d; thus, Equation 3 in Example 1 is not actively employed. In addition, because expression data are not used in Equation 11, the weighting term $f_r$ in Equation 4g, determined in Equation 2, is less useful and has been omitted. This is equivalent to setting $f_r=1$ in (4g).

2.1.4 Determining Derived Strain Flux Distribution

MOMA (Segrè 2002) is used to calculate the fluxes of derived strains ($v_j$). In this example, all derived strains are single gene knockouts.

$$\min_{v, V^{enz}} \sum_{j \in J} (w_j - v_j)^2 \tag{12a}$$

$$\text{S.T.} \sum_{i \in I} S_{i,j} \cdot v_j = 0 \quad \forall j \in J \tag{12b}$$

$$v_j \geq 0 \quad \forall j \in J^{irr} \tag{12c}$$

$$-\sum_{n \in N(j)} V_{j,n}^{enz} \leq v_j \leq \sum_{n \in N(j)} V_{j,n}^{enz} \quad \forall j \in J_{GPR} \tag{12d}$$

-continued $$V_{j,n}^{enz} \geq 0 \quad \forall j \in J_{GPR}, n \in N(j) \tag{12e}$$

$$V_{j,n}^{enz} = 0 \quad \forall j \in J_{KO}, n \in N(j) \tag{12f}$$

2.1.5 Calculation of Error

Mean squared error (MSE) is used extensively as a metric for the quality of the fit to the experimentally measured intracellular fluxes from MFA data. For any particular strain, the difference between the predicted ($v_j$ or $w_j$) and measured ($v_j^{MFA}$ or $w_j^{MFA}$) flux is squared and summed over all of the measured fluxes. This is then normalized by the number of fluxes being compared.

$$MSE = \frac{\sum_{j \in J_{MFA}} (v_j - v_j^{MFA})^2}{\|J_{MFA}\|} \tag{13}$$

2.2 Results and Discussion

The methods outlined in Example 1 utilize gene expression data or proteomics data. However, further analysis of the published dataset (Ishii et al. 2007) indicated that the relative levels of both genes and proteins did not sufficiently correlate to fluxes, and the gene expression data and enzyme contributions did not improve flux estimations. As a result, in this Example we tested REPPS without gene expression data and enzyme contributions. As in Example 1, we utilized the dataset from (Ishii et al. 2007), which contains measured extracellular fluxes, intracellular fluxes (MFA data), gene expression, and protein levels for 24 single gene knockouts as well as the parental strain grown in a chemostat. We utilized this data to test the predicted flux distributions from REPPS against the reported MFA data for the parental strain, reference strains, and derived strains.

2.2.1 Estimation of Reference Strain Flux Distributions

Figure 6:
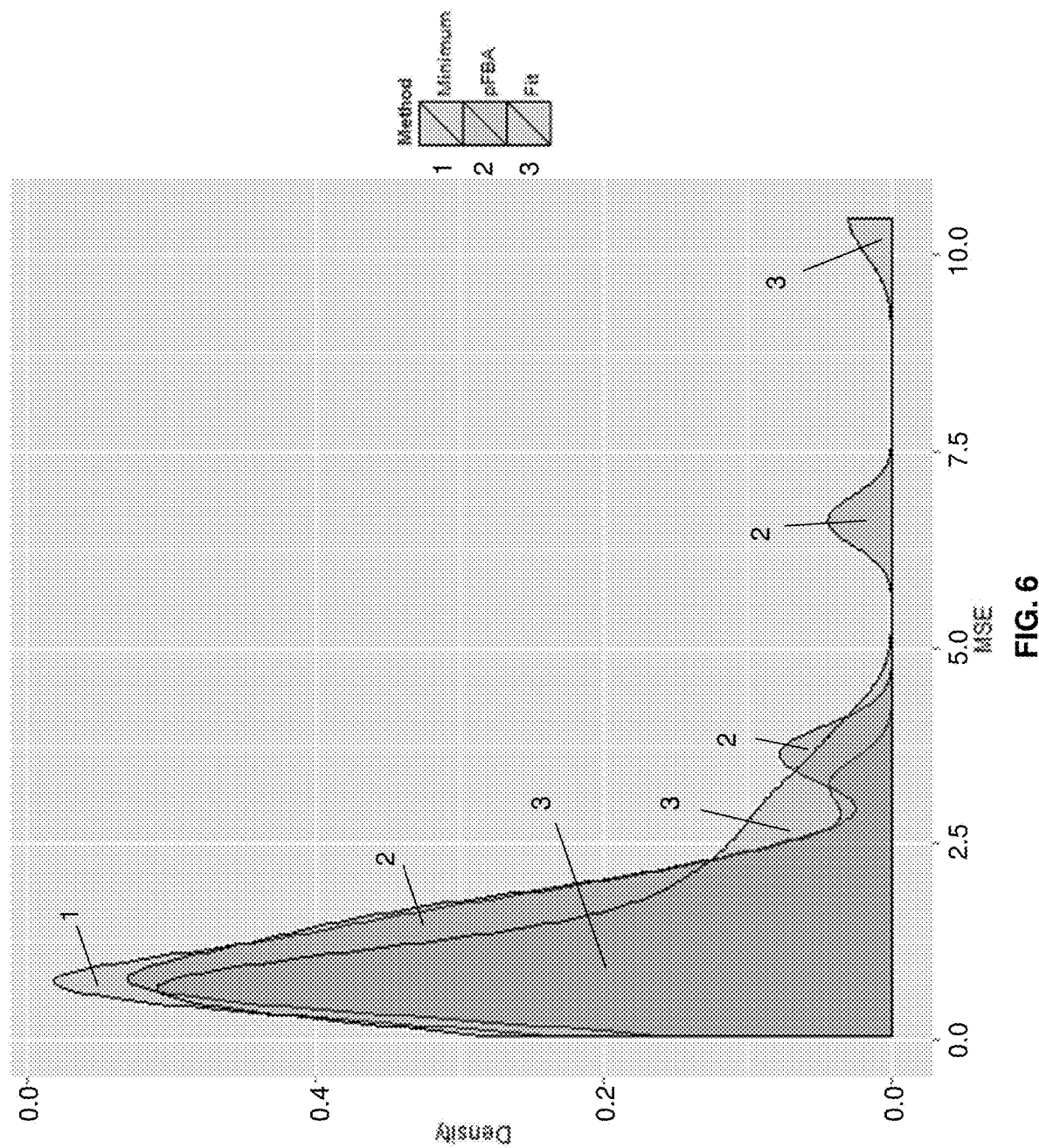
FIG. 6 shows the density of the mean squared error (MSE) of the predicted fluxes vs the measured intracellular fluxes for various methods of calculating the reference strain flux distributions. Data from 24 mutant strains and their parental strain were used. The minimum possible error obtained by minimizing the MSE is indicated. The Fit function had a median lower than pFBA. However, it also contained more results with higher MSEs.

We estimated the flux distributions for all 24 mutants and the parental strain utilizing pFBA, the Fit method, and the minimization of the possible error as a control (representing the best case scenario). We then calculated the mean-squared error (MSE) between the predicted flux values and the measured MFA and extracellular fluxes (FIG. 6). Overall, both pFBA and the Fit method proved to be similarly accurate. The average MSE across all strains was 1.48 for pFBA and 1.52 for the Fit as compared to 1.10 mmol$^2$/(gDW*hr)$^2$ for the minimum possible error. Conversely, the median MSE was 1.09 for pFBA, 0.78 for the Fit, and 0.55 mmol$^2$/(gDW*hr)$^2$ for the minimum. Therefore, while the Fit function appears to be more accurate than pFBA for the majority of strains, it results in a higher quantity and range of outliers that could potentially bias the REPPS formulation. Since it was not apparent which method would be more effective for calculating the reference strain estimations, we used both pFBA and Fit to predict reference strain fluxes in REPPS and then compared them.

2.2.2 Determination of Parental Strain Flux Distributions

Figure 7:
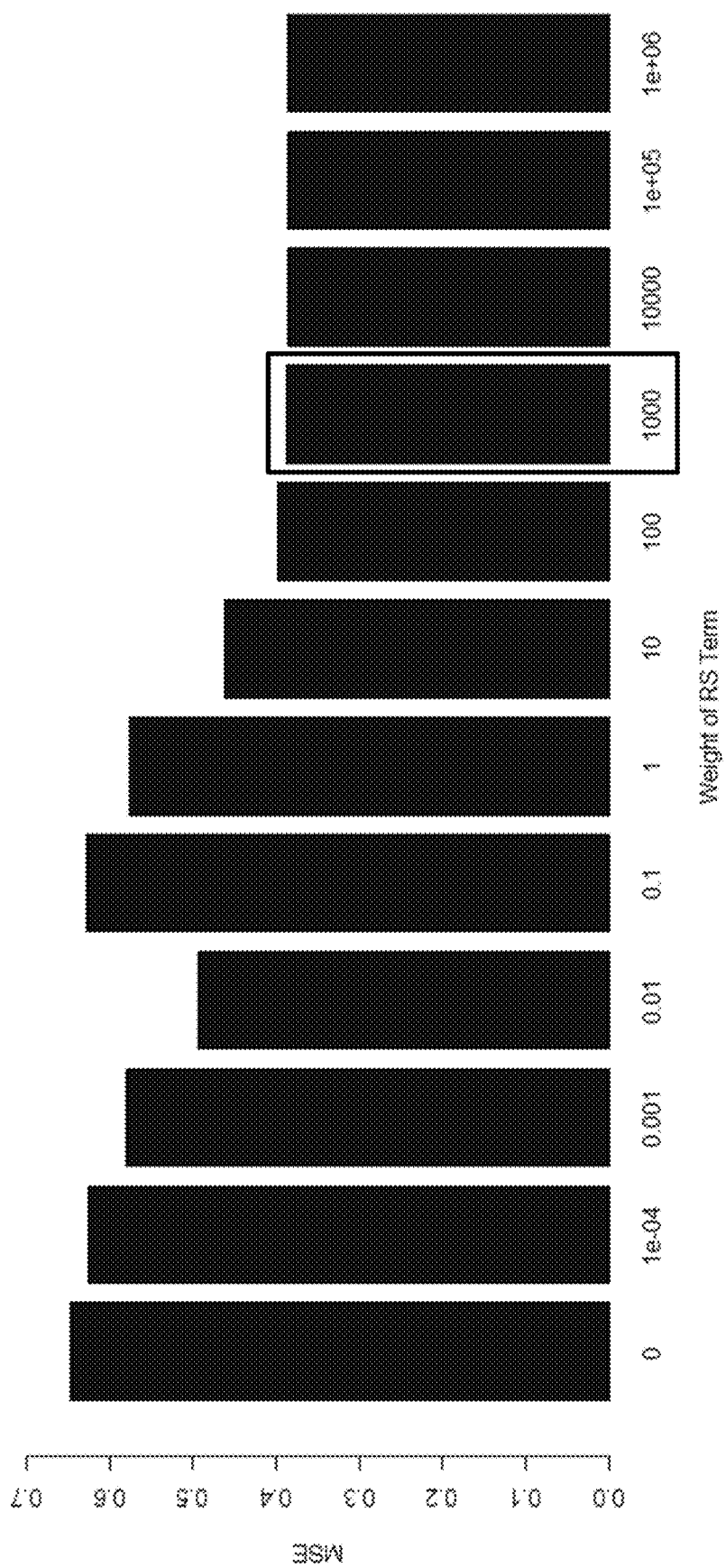
FIG. 7 shows a plot of MSE vs a weighting factor ($\gamma$) utilizing 24 reference strains using the Fit function. As $\gamma$ is increased, the reference strains are fit better at the expense of exactly fitting the extracellular fluxes. At a sufficiently high value ($\gamma=1000$), the results stabilized at their lowest MSE.

Before using REPPS, we determined the appropriate weighting (β) of the reference strain term relative to the extracellular flux term. After performing REPPS utilizing the full reference strain dataset of 24 mutants with values of β ranging from 0 to 1,000,000, it was determined that β should have a value of 1,000 to best predict the measured flux distribution (FIG. 7). This is equivalent to β=1000 and α=1 in Equation 4. It is important to note that the REPPS formulation normalizes each term. Since the extracellular flux term is divided by the number of extracellular flux measurements and the reference strain term is divided by the total number of reaction fluxes and reference strains, a value of 1000 for β effectively re-scales the term so that the absolute number of reactions is used for both terms. This is because there are on the order of 100 times the number of total reactions as those fluxes measured extracellularly.

Figure 8A:
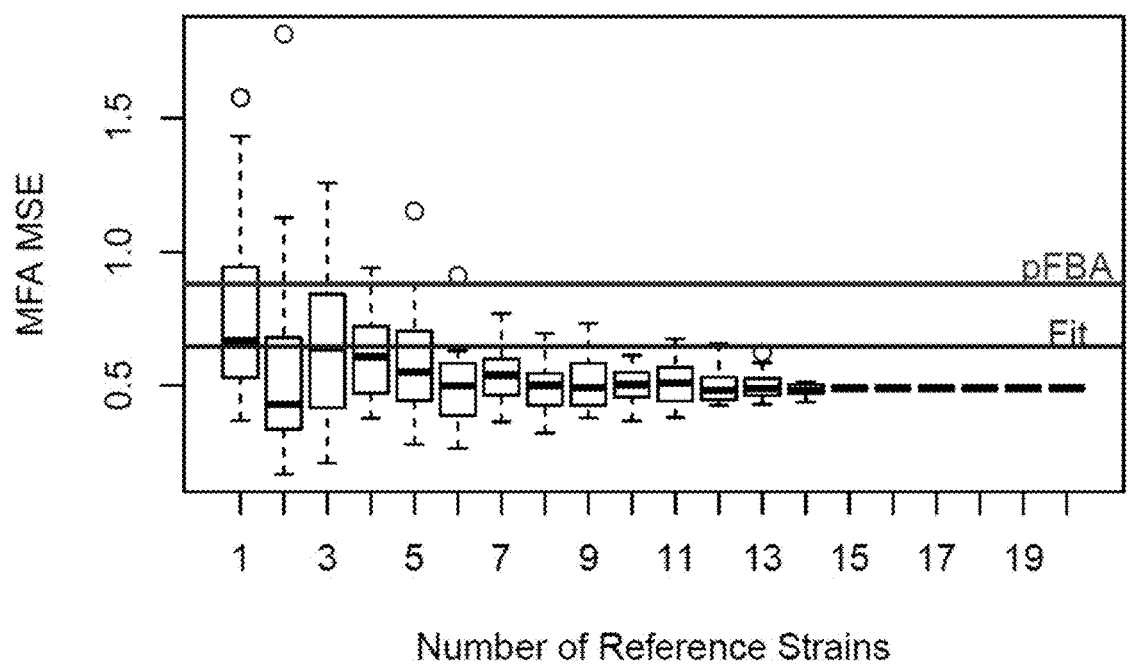
FIGS. 8A and 8B show the MSE for a parental strain calculated using MFA data. Plots utilize pFBA (FIG. 8A) or the Fit function (FIG. 8B) for estimating the reference strain flux distributions. For each column, a random subset of the specified size was selected from a 24 mutant pool. The PS flux distribution was then calculated using methods of the invention. This process was repeated for 20 times for each number of reference strains. The MSE for the parental strain found utilizing pFBA and the Fit function are indicated with the horizontal lines.
Figure 8B:
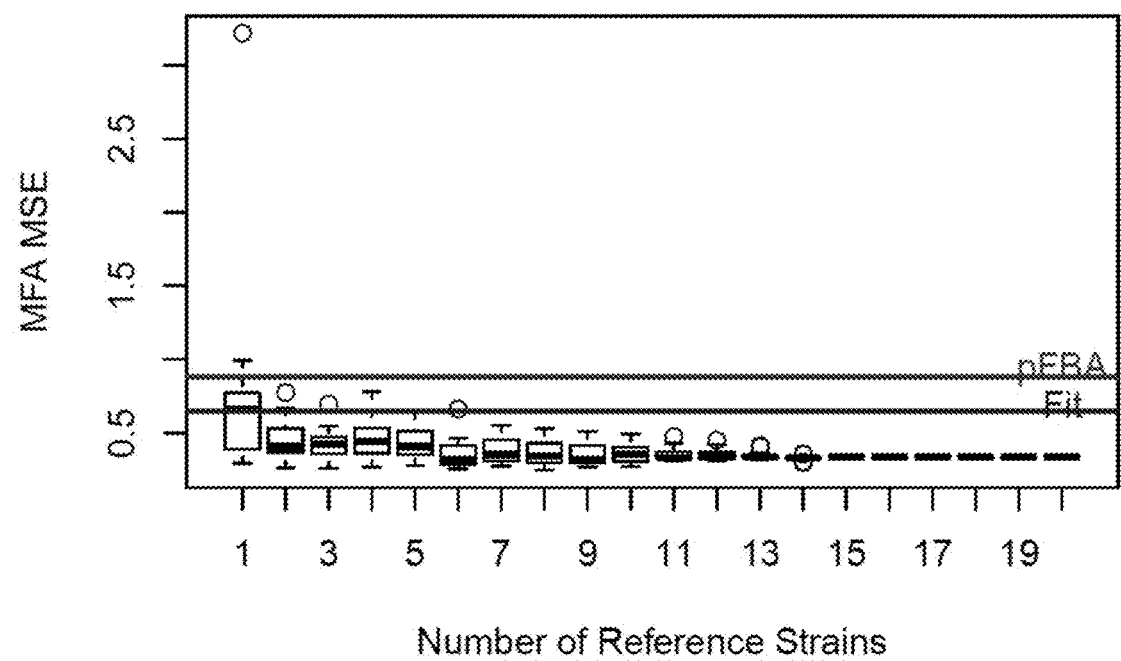

Once the weighting (β) has been specified, it is possible to calculate the parental strain flux distribution utilizing a varying number of reference strains (FIGS. 8A and 8B). By randomly sampling a set number of reference strains from the available pool of 24 knockouts, we can estimate the distribution of, and quality of, parental strain flux predictions. Regardless of whether pFBA or Fit is utilized for the reference strains, REPPS can improve the quality of parental strain flux estimations compared to those estimated by pFBA or the Fit method alone. Overall, the Fit method with REPPS results in a lower median and average MSE and converges to a lower MSE as more reference strains are incorporated. The Fit method does appear to make REPPS susceptible to extreme outliers when a low number of reference strains are used. However, the usage of two to three reference strains greatly reduces the chance of an outlier, and the usage of five or more reference strains appears to limit the parental strain estimation to be no worse than that predicted by the Fit method alone and often substantially improved (depending on which set of reference strains were randomly chosen). In fact, REPPS with five reference strains results in a median MSE of 0.41, while additional reference strains converge to a MSE of 0.34. Compared to the Fit function which results in a MSE of 0.65, REPPS improves the result by 37% and 48% respectively. Utilizing pFBA for the reference strain estimation in REPPS uniformly increased the error over the Fit reference strains with REPPS. pFBA reference strains both increased the number of outliers (although they were less severe than the worst outliers using the Fit method) and the median error for any number of reference strains. For example, five reference strains with pFBA resulted in a median MSE of 0.55 while incorporating more reference strains converged to a MSE of 0.49. Overall, it is clear that the Fit method for reference strain fitting performs better than the analogous pFBA method when used along with REPPS to predict parental strain fluxes. Utilizing the Fit method, REPPS can improve the parental strain estimation by nearly 50% compared to the pFBA estimation of the parental strain.

2.2.3 Prediction of Flux Distribution in Derived Strains

Figure 9:
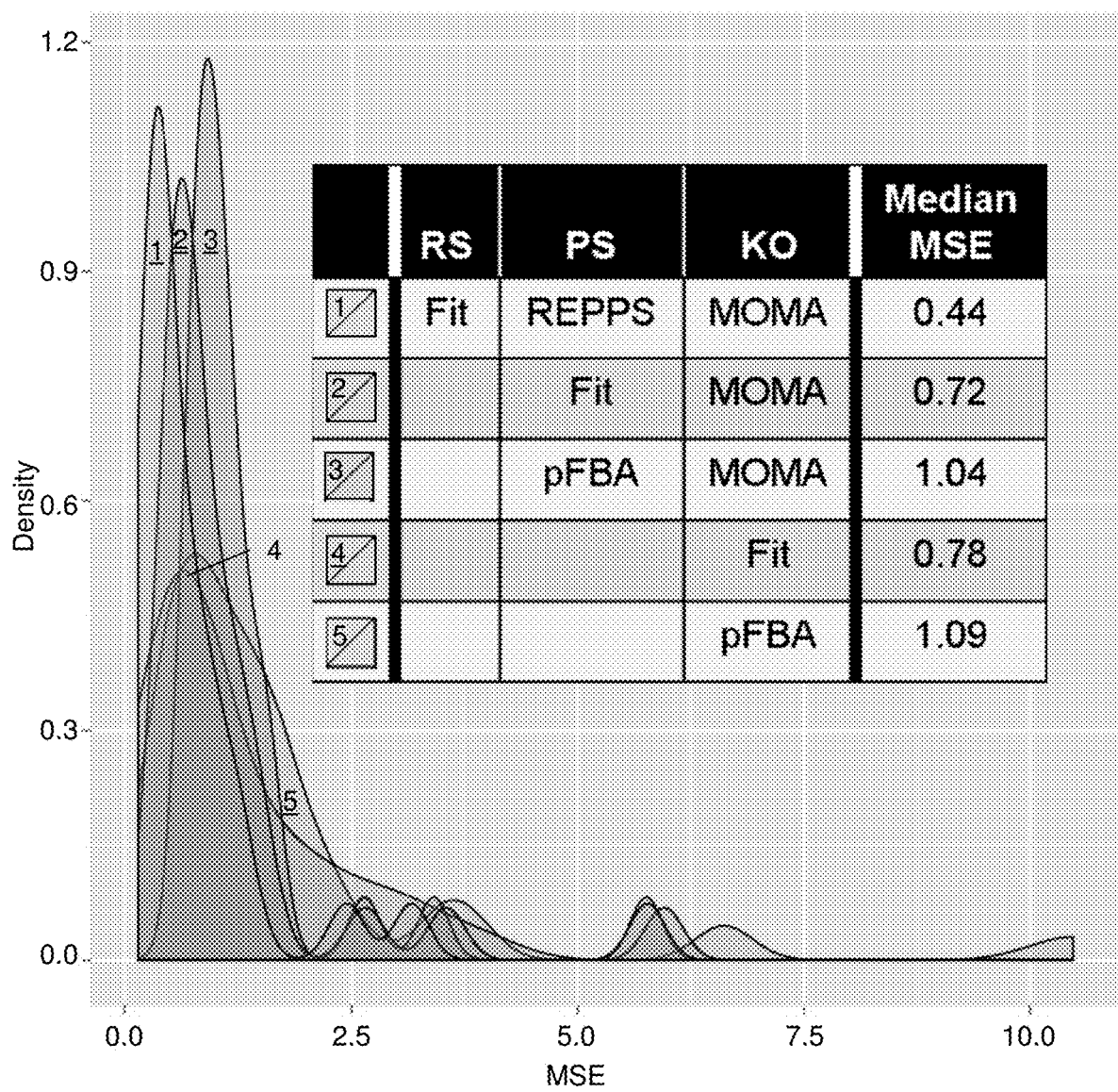
FIG. 9 shows the MSE density function utilizing various methods for calculating derived strains of single gene knockouts. The median MSE is shown for each method in the inserted table.

While REPPS is effective at improving the parental strain flux estimation, for strain design applications it is pertinent to see whether more accurate parental strain flux estimates improves flux predictions in strains derived from the parental strains (referred to here as derived strains). To test this, used the parental strain flux estimates generated by REPPS, using Δpgm, Δpgi, ΔpfkB, ΔppsA, and Δzwf data as the reference strains, to predict fluxes in the 19 other single gene knockouts using MOMA, which form the set of derived strains. This particular set of reference strains was chosen since it gave the median MSE, when considering all randomly tested sets of 5 reference strains. As a control, we also calculated the flux distributions for the 19 single gene knockouts utilizing pFBA and the Fit method with their measured extracellular fluxes, as well as MOMA from a parental flux estimate from pFBA or the Fit method. A comparison of the MSE distributions shows that utilizing REPPS' parental fluxes results in the lowest error for derived strain fluxes and has substantially fewer outliers than alternative control methods (FIG. 9). Interestingly, REPPS did better at predicting fluxes in derived strains (median MSE=0.44) than methods that used experimental measurements for the derived strains—pFBA and Fit (median MSE=1.09 and 0.78, respectively). By utilizing REPPS with five reference strains for the parental strain estimation and MOMA for the derived strain estimation, the median MSE of the 19 remaining knockouts was 0.44, a 58% improvement over the 1.04 median MSE predicted using the more traditional approach of using pFBA to estimate parental fluxes and MOMA to predict derived strain fluxes. Overall, this analysis indicates that the more accurate parental strain flux estimates generated by REPPS improves flux predictions for strains derived from the parental strain.

CONCLUSIONS

REPPS significantly improves parental strain flux distribution predictions without using MFA data or even gene expression data. Improved parental strain flux distributions further improves flux predictions in knockout mutants that are derived from the parental strain and which are not part of the reference set used to estimate the parental strain flux distribution.

REFERENCES

Becker S A, Palsson B O. Context-specific metabolic networks are consistent with experiments. Sauro H M, editor. *PLoS Comput Biol*. Public Library of Science; 2008 May; 4(5):e1000082.

Blazier A S, Papin J A. Integration of expression data in genome-scale metabolic network reconstructions. *Front Physiol*. 2012 Aug. 6; 3:299.

Burgard A P, Nikolaev E V, Schilling C H, Maranas C D. Flux coupling analysis of genome-scale metabolic network reconstructions. *Genome Res*. Cold Spring Harbor Laboratory Press; 2004 Mar. 1; 14(2):301-12.

Chandrasekaran S, Price N D. Probabilistic integrative modeling of genome-scale metabolic and regulatory networks in *Escherichia coli* and *Mycobacterium tuberculosis*. *Proc Natl Acad Sci USA*. 2010 Oct. 12; 107(41):17845-50.

Chowdhury A, Zomorrodi A R, Maranas C D. k-OptForce: integrating kinetics with flux balance analysis for strain design. *PLoS Comput Biol*. 2014 Feb. 20; 10(2): e1003487.

Covert M W, Xiao N, Chen T J, Karr J R. Integrating metabolic, transcriptional regulatory and signal transduction models in *Escherichia coli*. *Bioinformatics*. 2008 Sep. 15; 24(18):2044-50.

Griffin T J. Complementary Profiling of Gene Expression at the Transcriptome and Proteome Levels in *Saccharomyces cerevisiae*. *Mol Cell Proteomics*. 2002 Apr. 2; 1(4): 323-33.

Ishii N, Nakahigashi K, Baba T, Robert M, Soga T, Kanai A, Hirasawa T, Naba M, Hirai K, Hoque A, Ho P Y, Kakazu Y, Sugawara K, Igarashi S, Harada S, Masuda T, Sugiyama N, Togashi T, Hasegawa M, Takai Y, Yugi K, Arakawa K, Iwata N, Toya Y, Nakayama Y, Nishioka T, Shimizu K, Mori H, Tomita M. Multiple high-throughput analyses monitor the response of *E. coli* to perturbations. *Science*. 2007 Apr. 27; 316(5824):593-7.

Kim J, Reed J L. RELATCH: relative optimality in metabolic networks explains robust metabolic and regulatory responses to perturbations. *Genome Biol*. 2012 Jul. 5; 13(9):R78.

Kim H U, Sohn S B, Lee S Y. Metabolic network modeling and simulation for drug targeting and discovery. *Biotechnol J*. 2012 Mar. 29; 7(3):330-42.

Lewis N E, Hixson K K, Conrad T M, Lerman J A, Charusanti P, Polpitiya A D, Adkins J N, Schramm G, Purvine S O, Lopez-Ferrer D, Weitz K K, Eils R, Konig R, Smith R D, Palsson B Ø. Omic data from evolved *E. coli* are consistent with computed optimal growth from genome-scale models. *Mol Syst Biol.* 2010 July; 6:390.

Liu T, Zou W, Liu L, Chen J. A constraint-based model of *Scheffersomyces stipitis* for improved ethanol production. *Biotechnol Biofuels.* BioMed Central; 2012 Sep. 21; 5(1): 72.

Machado D, Herrgard M. Systematic evaluation of methods for integration of transcriptomic data into constraint-based models of metabolism. Maranas C D, editor. *PLoS Comput Biol.* Public Library of Science; 2014 April; 10(4):e1003580.

Mahadevan R, Schilling C H. The effects of alternate optimal solutions in constraint-based genome-scale metabolic models. *Metab Eng.* 2003; 5(4):264-76.

Montezano D, Meek L, Gupta R, Bermudez L E, Bermudez J C M. Flux Balance Analysis with Objective Function Defined by Proteomics Data—Metabolism of *Mycobacterium tuberculosis* Exposed to Mefloquine. Bourdon J, editor. *PLoS One.* Public Library of Science; 2015 Jul. 28; 10(7):e0134014.

Orth J D, Conrad T M, Na J, Lerman J A, Nam H, Feist A M, Palsson B. A comprehensive genome-scale reconstruction of *Escherichia coli* metabolism—2011. *Mol Syst Biol.* 2011 Oct. 11; 7:535.

Orth J D, Thiele I, Palsson B Ø. What is flux balance analysis? *Nat Biotechnol.* Nature Publishing Group; 2010 March; 28(3):245-8.

Reed J L, Vo T D, Schilling C H, Palsson B Ø. An expanded genome-scale model of *Escherichia coli* K-12 (iJR904 GSM/GPR). *Genome Biol.* 2003; 4(9):R54.

Segrè D, Vitkup D, Church G M. Analysis of optimality in natural and perturbed metabolic networks. *Proc Natl Acad Sci USA.* 2002 Nov. 12; 99(23):15112-7.

Shlomi T, Berkman O, Ruppin E. Regulatory on/off minimization of metabolic flux changes after genetic perturbations. Proc Natl Acad Sci USA. 2005 May 24; 102(21): 7695-700.

Zamboni N, Fendt S-M, Ruhl M, Sauer U. $^{13}$C-based metabolic flux analysis. *Nat Protoc.* 2009 January; 4(6): 878-92.

What is claimed is:

1. A method for determining flux distribution in a parental strain and in a derived strain thereof, comprising:
generating a plurality of reference strains, each reference strain having a known genetic modification with respect to the parental strain;
experimentally measuring extracellular fluxes for each of the plurality of reference strains;
estimating, in a computer system, a flux distribution from the experimentally measured extracellular fluxes for each of the plurality of reference strains, wherein the flux distribution for each reference strain comprises a directional, quantitative set of fluxes corresponding to a set of reactions occurring in the reference strain;
experimentally measuring extracellular fluxes from the parental strain;
determining, in a computer system, a flux distribution for the parental strain from the estimated flux distributions for the reference strains and the experimentally measured extracellular fluxes for the parental strain, wherein the flux distribution for the parental strain comprises a directional, quantitative set of fluxes corresponding to a set of reactions occurring in the parental strain;
predicting, from the flux distribution determined for the parental strain, a flux distribution for an uncharacterized strain having a genetic modification with respect to the parental strain, wherein the uncharacterized strain is not one of the reference strains; and
generating the uncharacterized strain.

2. A method for determining flux distribution in a parental strain and in a derived strain thereof, comprising:
estimating, in a computer system, a flux distribution from experimentally measured extracellular fluxes for each of a plurality of reference strains, each reference strain having a known genetic modification with respect to the parental strain, wherein the flux distribution for each reference strain comprises a directional, quantitative set of fluxes corresponding to a set of reactions occurring in the reference strain, wherein the estimating the flux distribution for each of the reference strains is performed without metabolic flux analysis data for any of the reference strains and without experimentally measured gene expression data for any of the reference strains;
determining, in a computer system, a flux distribution for the parental strain from the estimated flux distributions for the reference strains and experimentally measured extracellular fluxes for the parental strain, wherein the flux distribution for the parental strain comprises a directional, quantitative set of fluxes corresponding to a set of reactions occurring in the parental strain, wherein the determining the flux distribution for the parental strain is performed without metabolic flux analysis data for the parental strain and without experimentally measured gene expression data for the parental strain;
predicting, from the flux distribution determined for the parental strain, a flux distribution for an uncharacterized strain having a genetic modification with respect to the parental strain, wherein the uncharacterized strain is not one of the reference strains; and
generating the uncharacterized strain.

3. A method for determining flux distribution in a parental strain and in a derived strain thereof, comprising:
estimating, in a computer system, a flux distribution from experimentally measured extracellular fluxes for each of a plurality of reference strains, each reference strain having a known genetic modification with respect to the parental strain, wherein the flux distribution for each reference strain comprises a directional, quantitative set of fluxes corresponding to a set of reactions occurring in the reference strain;
determining, in a computer system, a flux distribution for the parental strain from the estimated flux distributions for the reference strains and experimentally measured extracellular fluxes for the parental strain, wherein the flux distribution for the parental strain comprises a directional, quantitative set of fluxes corresponding to a set of reactions occurring in the parental strain;
predicting, from the flux distribution determined for the parental strain, a flux distribution for an uncharacterized strain having a genetic modification with respect to the parental strain, wherein the uncharacterized strain is not one of the reference strains; and
generating the uncharacterized strain.

* * * * *